(12) United States Patent
Urakawa et al.

(10) Patent No.: US 9,981,112 B2
(45) Date of Patent: May 29, 2018

(54) CAMERA SYSTEM FOR MONITORING INSIDE OF BODY, ACCESSORY FOR SUPPORT TUBE OF CAMERA SYSTEM FOR MONITORING INSIDE OF BODY, FIXING TOOL FOR CAMERA SYSTEM FOR MONITORING INSIDE OF BODY, AND METHOD FOR INSTALLING CAMERA SYSTEM FOR MONITORING INSIDE OF BODY

(71) Applicant: Sharp Kabushiki Kaisha, Osaka-shi, Osaka (JP)

(72) Inventors: Kei Urakawa, Osaka (JP); Toshihisa Gotoh, Osaka (JP); Tsuguhisa Inoue, Osaka (JP); Kishoh Takamatsu, Osaka (JP); Hitoshi Aoki, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days. days.

(21) Appl. No.: 15/031,816

(22) PCT Filed: Dec. 1, 2014

(86) PCT No.: PCT/JP2014/081790
§ 371 (c)(1),
(2) Date: Apr. 25, 2016

(87) PCT Pub. No.: WO2015/080293
PCT Pub. Date: Jun. 4, 2015

(65) Prior Publication Data
US 2016/0263350 A1    Sep. 15, 2016

(30) Foreign Application Priority Data
Nov. 29, 2013  (JP) .................................. 2013-248565

(51) Int. Cl.
*A61B 1/00* (2006.01)
*A61M 25/02* (2006.01)
(Continued)

(52) U.S. Cl.
CPC ......... *A61M 25/02* (2013.01); *A61B 1/00006* (2013.01); *A61B 1/00045* (2013.01);
(Continued)

(58) Field of Classification Search
USPC .................................. 600/114, 121–125, 154
See application file for complete search history.

(56) References Cited

U.S. PATENT DOCUMENTS

| 5,855,569 | A | * | 1/1999 | Komi | ..................... | A61B 10/04 |
| | | | | | | 604/103 |
| 7,226,411 | B2 | * | 6/2007 | Akiba | ..................... | A61B 1/018 |
| | | | | | | 600/104 |

(Continued)

FOREIGN PATENT DOCUMENTS

| JP | 05-115423 A | 5/1993 |
| JP | 2009-072368 A | 4/2009 |

(Continued)

OTHER PUBLICATIONS

Aoki et al., "Camera System for Monitoring Inside of Body", U.S. Appl. No. 15/546,291, filed Jul. 26, 2017.
(Continued)

*Primary Examiner* — Matthew J Kasztejna
(74) *Attorney, Agent, or Firm* — Keating & Bennett, LLP

(57) ABSTRACT

A camera system (1) for monitoring the inside of a body (1), includes: a camera support tube (13) of which one end part (13a) is inserted into the body; a camera unit (11) which joins with the support tube inside the body; a camera side cable (12) which is connected to the camera unit, and is drawn out toward the outside of the body through the camera
(Continued)

support tube; a control system (3) which includes at least a display (18); and a string-like member (38) which directly or indirectly fixes the camera support tube to the body surface.

9 Claims, 23 Drawing Sheets

(51) Int. Cl.
*A61B 1/313* (2006.01)
*A61B 90/00* (2016.01)
*A61B 1/04* (2006.01)
*A61B 17/00* (2006.01)
*A61B 17/34* (2006.01)
*A61B 90/11* (2016.01)

(52) U.S. Cl.
CPC ...... *A61B 1/00114* (2013.01); *A61B 1/00147* (2013.01); *A61B 1/04* (2013.01); *A61B 1/3132* (2013.01); *A61B 90/361* (2016.02); *A61B 90/11* (2016.02); *A61B 2017/00283* (2013.01); *A61B 2017/00477* (2013.01); *A61B 2017/3447* (2013.01); *A61M 2025/024* (2013.01); *A61M 2025/028* (2013.01); *A61M 2025/0253* (2013.01); *A61M 2025/0286* (2013.01)

(56) References Cited

U.S. PATENT DOCUMENTS

| | | | | |
|---|---|---|---|---|
| 7,448,993 | B2* | 11/2008 | Yokoi | A61B 1/273 600/101 |
| 8,348,828 | B2* | 1/2013 | Asada | A61B 1/00147 600/104 |
| 2004/0133076 | A1* | 7/2004 | Kobayashi | A61B 1/00016 600/175 |
| 2007/0161855 | A1 | 7/2007 | Mikkaichi et al. | |
| 2007/0255100 | A1 | 11/2007 | Barlow et al. | |
| 2008/0015413 | A1* | 1/2008 | Barlow | A61B 1/00105 600/114 |
| 2008/0309758 | A1 | 12/2008 | Karasawa et al. | |
| 2010/0113872 | A1 | 5/2010 | Asada et al. | |
| 2011/0046440 | A1 | 2/2011 | Asada et al. | |

FOREIGN PATENT DOCUMENTS

| | | |
|---|---|---|
| JP | 4472727 B2 | 6/2010 |
| JP | 4599474 B1 | 12/2010 |
| JP | 2012-239519 A | 12/2012 |
| WO | 2007/078003 A1 | 7/2007 |
| WO | 2015/020124 A1 | 2/2015 |

OTHER PUBLICATIONS

Gotoh et al., "In-Body Monitoring Camera System and Support Tube for In-Body Monitoring-Camera-System", U.S. Appl. No. 14/899,269, filed Dec. 17, 2015.

Inoue et al., "In-Vivo Monitoring Camera System, and Support Tube for In-Vivo Monitoring Camera System", U.S. Appl. No. 15/031,777, filed Apr. 25, 2016.

Urakawa et al., "Intracorporeal-Monitoring Camera System, Support Tube for Intracorporeal-Monitoring Camera System, and Cable Holder for Intracorporeal-Monitoring Camera System", U.S. Appl. No. 14/917,064, filed Mar. 7, 2016.

Aoki et al., "Camera System for Monitoring Inside of Body and Auxiliary Device and Method for Installing Imaging Apparatus for Monitoring Inside of Body", U.S. Appl. No. 15/111,514, filed Jul. 14, 2016.

Aoki et al., "In-Body Monitoring Camera System and Camera Unit", U.S. Appl. No. 15/129,044, filed Sep. 26, 2016.

Aoki et al., "Camera System for Monitoring Inside of Body and Auxiliary Tool Set", U.S. Appl. No. 15/112,726, filed Jul. 20, 2016.

* cited by examiner

| | |
|---|---|
| 1: CAMERA SYSTEM FOR MONITORING INSIDE OF BODY | 16: INSTRUMENT SIDE CABLE |
| | 16a: INSTRUMENT SIDE CABLE CONNECTOR |
| 3: CONTROL SYSTEM | 17: CAMERA UNIT CONTROL INSTRUMENT |
| 11: CAMERA UNIT | 18: DISPLAY |
| 12: CAMERA SIDE CABLE | 31: CANNULA |
| 12a: CAMERA SIDE CABLE CONNECTOR | 32: TROCAR |
| 13: CAMERA SUPPORT TUBE | 38: STRING-LIKE MEMBER |
| 13a: END PART | 41: BODY WALL |
| 13b: END PART | 45: BODY SURFACE |
| 14: SUPPORT TUBE JOINING PORTION | |

1: CAMERA SYSTEM FOR MONITORING INSIDE OF BODY
11: CAMERA UNIT
12: CAMERA SIDE CABLE
12a: CAMERA SIDE CABLE CONNECTOR
13: CAMERA SUPPORT TUBE
16: INSTRUMENT SIDE CABLE
16a: INSTRUMENT SIDE CABLE CONNECTOR
17: CAMERA UNIT CONTROL INSTRUMENT
18: DISPLAY
31: CANNULA
32a TO 32c: TROCAR
33a TO 33c: FORCEPS
34: ENDOSCOPE
38: STRING-LIKE MEMBER
41: BODY WALL
42: ORGAN
45: BODY SURFACE
117: ENDOSCOPE CONTROL INSTRUMENT
118: DISPLAY

12: CAMERA SIDE CABLE
12a: CAMERA SIDE CABLE CONNECTOR
13: CAMERA SUPPORT TUBE
31: CANNULA
41d: PORT
45: BODY SURFACE
141: FIXING DEVICE
144: SUPPORT TABLE
145: BAND
145a: FIXING END
146: ADJUSTER

12: CAMERA SIDE CABLE
12a: CAMERA SIDE CABLE CONNECTOR
13: CAMERA SUPPORT TUBE
31: CANNULA
45: BODY SURFACE
151: FIXING DEVICE
152: SUPPORT TABLE
153: CLIP PORTION
154: SUPPORT TUBE MOUNTING UNIT
155: ARM PORTION
156: CLAMP PORTION
157: SCREW FASTENING HANDLE

12: CAMERA SIDE CABLE
12a: CAMERA SIDE CABLE CONNECTOR
13: CAMERA SUPPORT TUBE
31: CANNULA
45: BODY SURFACE
161: FIXING DEVICE
162: SUPPORT TABLE
163: SUPPORT TUBE MOUNTING UNIT
164: ARM PORTION
165: CLAMP PORTION
166: SCREW FASTENING HANDLE

12: CAMERA SIDE CABLE
13: CAMERA SUPPORT TUBE
31: CANNULA
45: BODY SURFACE
49: RESTORING FORCE
50: BODY WALL PRESSING FORCE
171: FIXING DEVICE
172: ARM PORTION
173: CLAMP PORTION
174: LINKING PORTION

12: CAMERA SIDE CABLE
12a: CAMERA SIDE CABLE CONNECTOR
13: CAMERA SUPPORT TUBE
31: CANNULA
41d: PORT
45: BODY SURFACE
46: ADHESIVE TAPE

CAMERA SYSTEM FOR MONITORING INSIDE OF BODY, ACCESSORY FOR SUPPORT TUBE OF CAMERA SYSTEM FOR MONITORING INSIDE OF BODY, FIXING TOOL FOR CAMERA SYSTEM FOR MONITORING INSIDE OF BODY, AND METHOD FOR INSTALLING CAMERA SYSTEM FOR MONITORING INSIDE OF BODY

TECHNICAL FIELD

The present invention relates to a camera system for monitoring the inside of a body provided with an imaging unit which can be inserted into a body, an accessory for a support tube of a camera system for monitoring the inside of a body, a fixing tool for a camera system for monitoring the inside of a body, and a method for installing a camera system for monitoring the inside of a body.

BACKGROUND ART

Endoscopic surgery is minimally invasive surgery for performing examination or medical treatment without laparotomy with respect to a patient. In the endoscopic surgery, a treatment tool, such as forceps, and an endoscope are separately inserted into a body cavity of the patient, and a practitioner captures an image of a tip end part of the treatment tool inserted into the body cavity within an observation visual field of the endoscope, and performs the treatment operation while observing a treatment state of the patient by the treatment tool using the endoscope. In the endoscopic surgery, the treatment tool and the endoscope are inserted into the body cavity through a pipe punctured through a body wall (for example, an abdominal wall) in an abdomen or the like of the patient. In addition, the pipe is a tube-like member which is a so-called trocar.

The practitioner enlarges the image by making the endoscope approach an organ, and performs incision or suturing of the organ, but at this time, the visual field of the practitioner becomes extremely narrow. Therefore, an apparatus which can widely grasp a state (for example, the movement of the treatment tool, a bleeding state, and a remaining state of a residual, such as gauze, outside a work region) outside the work region, has been called for.

Corresponding to such a demand, in PTL 1, an apparatus which directly inserts a needle-like connector electrode into an abdominal wall, and joins the connector electrode and a camera to each other in a body, is disclosed.

In PTL 2, an apparatus which inserts a camera unit and a communication cable which joins with the camera unit from a trocar, draws out a needle and the communication cable from an abdominal wall hole toward the outside of a body in a state where an end part of the communication cable is hooked to the needle inserted from the abdominal wall hole, and fixes the communication cable, is disclosed.

CITATION LIST

Patent Literature

PTL 1: Japanese Patent No. 4472727 (issued on Jun. 2, 2010)
PTL 2: Japanese Patent No. 4599474 (issued on Dec. 15, 2010)

SUMMARY OF INVENTION

Technical Problem

However, in PTL 1, since the needle-like connector electrode is directly inserted into the abdominal wall and the connector electrode and the camera join with each other in the body, there is a concern that a foreign substance is mixed into a joining portion of the connector electrode and the camera, and an electric connection failure occurs.

In PTL 2, the communication cable is drawn out toward the outside of the body and fixed, but it is difficult to obtain joining strength between the communication cable and the camera unit due to characteristics of the communication cable, to change an orientation of the camera unit from the outside of the body, and to fix the camera unit in a state where the orientation thereof is changed.

In consideration of the above-described problems, an object of the present invention is to provide a camera system for monitoring the inside of a body which has high reliability and high usability, and a method for installing a camera system for monitoring the inside of a body.

Solution to Problem

In order to solve the above-described problems, there is provided a camera system for monitoring the inside of a body according to an aspect of the present invention, including: a support tube of which one end part is inserted into a body; an imaging unit which includes a joining portion which joins with the support tube, and joins with the support tube in the body; a cable which is connected to the imaging unit, and is drawn out toward the outside of the body through the support tube; a control system which is on the outside of the body, is connected to the cable, and includes at least a display apparatus; and a fixing tool which directly or indirectly fixes the support tube to a body surface in a state where a length of the support tube in the body, a rotational direction of the support tube, and an inclination of the support tube with respect to the body surface, which are set by a practitioner, are held.

In order to solve the above-described problems, there is provided a method for installing a camera system for monitoring the inside of a body according to another aspect of the present invention, including: a step of inserting a cable connected to a control system which has at least a display apparatus on the outside of the body, and an imaging unit connected to the cable, into the body; a step of drawing out the cable toward the outside of the body through a support tube of which one end part is inserted into the body; a step of joining the imaging unit and the support tube to each other at a joining portion provided in the imaging unit, in the body; and a step of adjusting a length of the support tube in the body, a rotational direction of the support tube, an inclination of the support tube with respect to the body surface, and directly or indirectly fixing the support tube to the body surface.

Advantageous Effects of Invention

According to one aspect of the present invention, it is possible to join the imaging unit to the support tube in the body in a state where the cable passes through the support tube. Therefore, a supporting force of the imaging unit is increased, the connection failure between the imaging unit and the cable is unlikely to occur, and reliability is high.

In addition, since the imaging unit joins with the support tube in the body, the practitioner can change the visual field direction of the imaging unit, the rotational direction of the visual field, and imaging zoom (distance to an object) in the body via the support tube.

Furthermore, by directly or indirectly fixing the support tube to the body surface in a state where the length of the support tube in the body, the rotational direction of the support tube, and the inclination of the support tube with respect to the body surface, which are set by the practitioner, are held, it is not necessary for the practitioner to support the support tube.

Therefore, according to the aspect of the present invention, it is possible to provide a camera system for monitoring the inside of a body which has high reliability and high usability, and a method for installing a camera system for monitoring the inside of a body.

DESCRIPTION OF EMBODIMENTS

Figure 1:
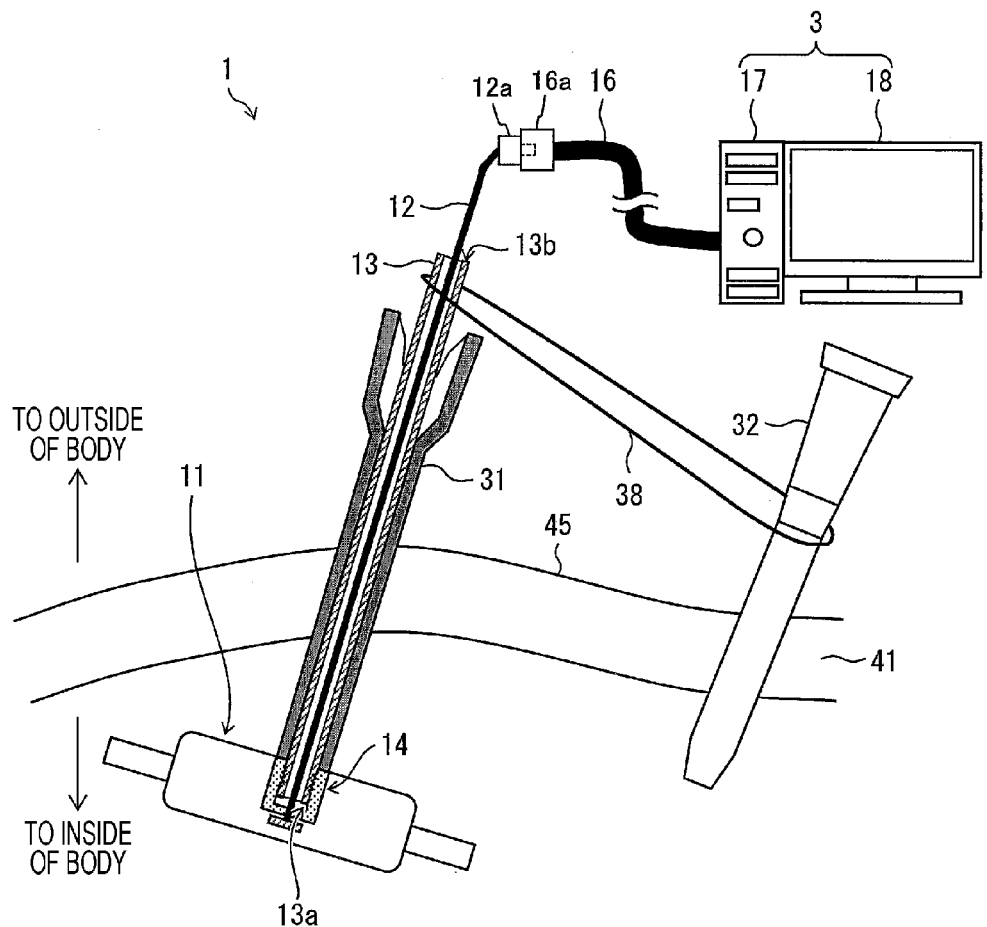
FIG. 1 is a schematic view illustrating a schematic configuration of a camera system for monitoring the inside of a body according to Embodiment 1.
Figure 2:
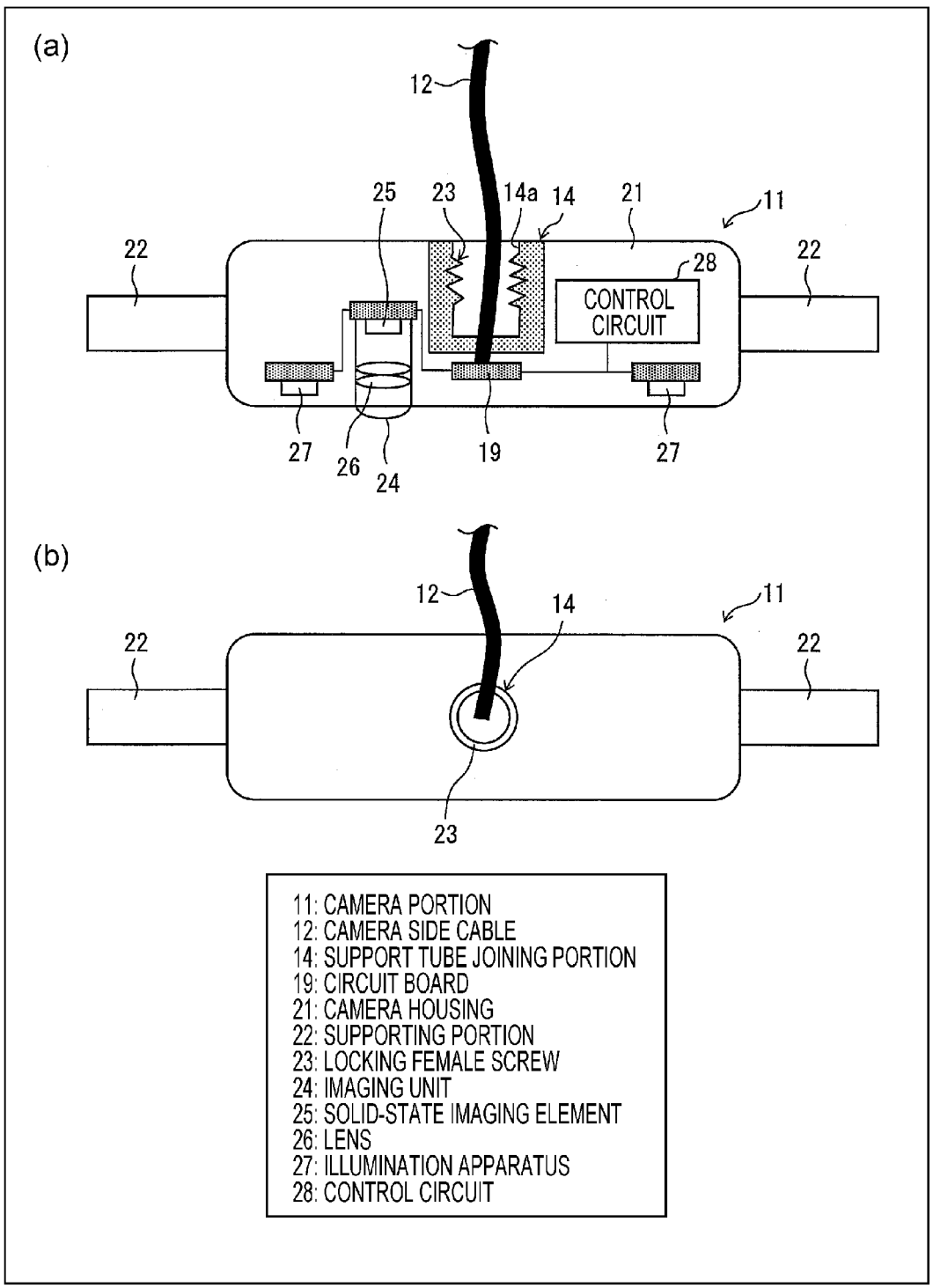
FIG. 2(a) is a sectional view schematically illustrating a schematic configuration of main parts of an imaging apparatus according to Embodiment 1.
FIG. 2(b) is an upper view of the imaging apparatus illustrated in FIG. 2(a).

An embodiment of the present invention will be described based on FIGS. 1 to 23 as follows. For convenience of description, members having the same functions as those of members illustrated in each embodiment will be given the same reference numerals, and detailed descriptions thereof will be appropriately omitted. In addition, the dimensions, such as the shape, the length, the size, and the width, of configurations described in each drawing do not reflect the real shape or dimensions, and are appropriately changed for making the drawings apparent and simple.

[Embodiment 1]

(Schematic Configuration of Camera System for Monitoring inside of Body)

FIG. 1 is a schematic view illustrating a schematic configuration of a camera system for monitoring the inside of a body 1 according to the embodiment.

As illustrated in FIG. 1, the camera system for monitoring the inside of a body 1 according to the embodiment includes a camera unit 11 (imaging unit), a camera side cable 12 of which one end is connected to the camera unit 11, a camera support tube 13 (support tube), a control system 3 including a camera unit control instrument 17 and a display 18 (display apparatus), a cannula 31 (cannula, holding tube), a string-like member 38 (fixing tool), and an instrument side cable 16 of which one end is connected to the camera unit control instrument 17. In addition, as a camera side cable connector 12a provided at the other end of the camera side cable 12, and an instrument side cable connector 16a provided at the other end of the instrument side cable 16, are fitted to each other, the camera unit 11 and the control system 3 are electrically connected to each other. Hereinafter, the camera side cable connector 12a will be referred to as a connector 12a, and the instrument side cable connector 16a will be referred to as a connector 16a.

(Camera Unit 11)

FIG. 2(a) is a sectional view schematically illustrating a schematic configuration of main parts of the camera unit 11 according to the embodiment. FIG. 2(b) is an upper view of the camera unit 11 illustrated in FIG. 2(a). In addition, an imaging apparatus is configured to include the camera unit 11 (imaging unit) which images the inside of a body, and the camera side cable 12 (cable) which is connected to the camera unit 11.

As illustrated in FIGS. 2(a) and 2(b), the camera unit 11 includes a camera housing 21, a circuit board 19, an imaging unit 24, a control circuit 28, an illumination apparatus 27, and a supporting portion 22.

The circuit board 19, the imaging unit 24, the control circuit 28, and the illumination apparatus 27 are provided in the camera housing 21. Meanwhile, the supporting portion 22 is provided on an outer side of the camera housing 21.

First, a configuration of the inside of the camera housing 21 will be described.

The imaging unit 24 is provided with a lens 26 which is an imaging lens, and a solid-state imaging device 25.

The solid-state imaging device 25 is disposed so that an optical axis of the lens 26 and an axial center match each other. Examples of the solid-state imaging device 25 include a charge-coupled device (CCD) and a complementary metal-oxide semiconductor (CMOS) image sensor.

The illumination apparatus 27 makes an image captured by the camera unit 11 clear by illuminating the inside of the body with light. It is preferable that the size of the illumination apparatus 27 is small, and a light emitting diode (LED) or the like can be appropriately used. In addition, in the camera unit 11, one illumination apparatus 27 may be provided, and a plurality of illumination apparatuses 27 may be provided as illustrated in FIG. 2(a).

The solid-state imaging device 25, the illumination apparatus 27, and the control circuit 28 are connected to the circuit board 19.

The control circuit 28 is electrically connected to the imaging unit 24 and the illumination apparatus 27 via the circuit board 19.

In addition, one end part of the camera side cable 12 is connected to the circuit board 19, and a signal is input and output between the circuit board 19 and the camera unit control instrument 17 in the control system 3 (refer to FIG. 1) via the camera side cable 12 and a connection unit 4 (refer to FIG. 1).

Accordingly, the control circuit 28 controls the driving of the imaging unit 24 and the illumination apparatus 27 based on a control signal input from the camera unit control instrument 17 via the camera side cable 12 and the circuit board 19.

Since a wired type is employed in transmission from the camera unit 11 to the camera unit control instrument 17, it is possible to increase a transmission speed, and send and receive the signal by stabilizing the signal, and thus, it is possible to obtain an image having high resolution. In addition, it is possible to perform communication at low power compared to a wireless type, and to decrease the size of the camera unit 11 by supplying power from the outside. Therefore, since it is possible to reduce damage when the camera unit 11 is inserted into the body due to the small size, there is an effect that low invasiveness is improved.

Next, the camera housing 21, and the supporting portion 22 provided on the outside of the camera housing 21, will be described.

The camera housing 21 includes a recessed support tube joining portion 14 (joining portion) on an upper surface thereof. The support tube joining portion 14 has an annular opening shape (hole structure) when viewed from above as illustrated in FIG. 2(a), and has a configuration in which a locking female screw 23 is provided on an inner wall of the opening as illustrated in FIG. 2(b).

In addition, the supporting portions 22 are provided to protrude to the outside from each of both opposing side surfaces in the camera housing 21.

The supporting portion 22 is used as a gripping unit in the camera unit 11. The camera unit 11 is inserted into the body through a trocar 32 (tube-like member, refer to FIG. 1). The supporting portion 22 is for supporting the camera unit 11. The supporting portion 22 is gripped when the camera unit 11 is inserted into the body from the trocar 32 using forceps, or is gripped so that an upper surface (a surface provided with the support tube joining portion 14) of the camera unit 11 faces an end part of the camera support tube 13 when the camera unit 11 and the camera support tube 13 join with each other. Accordingly, the supporting portion 22 can support the camera unit 11.

In addition, in the camera housing 21 of the camera unit 11, a part at which the lens 26 or the illumination apparatus 27 is disposed is configured of a transparent material, but it is desirable that a region (including the supporting portion 22) other than the part is configured of a blue or green material which is easily noticed inside the body. In this manner, by making a color inside a body which is red or yellow into a blue or green color that is a complementary color, it is possible to make visual recognition easy during installation work or withdrawing work inside the body, which will be described later. Accordingly, by making the camera unit 11 blue or green, there is an effect that the time for the installation work of the camera unit 11 can be shortened, and safety increases.

As described above, other than coloring with a blue or green material, a phosphorescent material or a reflecting material which is likely to be visually recognized may be used. In this manner, since it is possible to directly see the part in the shade of an organ that is unlikely to be visually recognized, or at an end of a visual field where illumination light is unlikely to reach, the phosphorescent material or the reflecting material is particularly effective.

(Camera Side Cable 12 and Instrument Side Cable 16)

The camera side cable 12 is a communication cable on a camera side, and the instrument side cable 16 is a communication cable on a camera unit control instrument side. The image captured by the camera unit 11 is sent to the camera unit control instrument 17 via the camera side cable 12 and the instrument side cable 16 as an image signal, and the control signal from the camera unit control instrument 17 is sent to the camera unit 11 via the instrument side cable 16 and the camera side cable 12.

One end part of the camera side cable 12 is connected to the circuit board 19, and is guided toward the outside of the camera unit 11 passing through the inside of the support tube joining portion 14. In addition, a connection part between the circuit board 19 and the camera side cable 12 is sealed by a resin or the like which is not illustrated. Furthermore, at a part (bottom unit of the recessed support tube joining portion 14) which is drawn out in the camera side cable 12 inside the support tube joining portion 14, the camera side cable 12 is adhered and fixed to the support tube joining portion 14. An example of the adhesion and fixing includes sealing and fixing by an adhesion or an O-ring. Intrusion of water and mixing of foreign materials into the camera unit 11 from the adhered and fixed part, are prevented.

As will be described later, the camera side cable 12 is inserted into a body cavity through the tube-like member, such as the trocar 32 (refer to FIG. 1) in a state of being connected to the camera unit 11, or is drawn out toward the outside of the body through the camera support tube 13 (refer to FIG. 1), which will be described later, and joins with the camera unit 11 via the support tube joining portion 14. Therefore, the camera side cable 12 is formed of a flexible material having flexibility.

In addition, in the description above, it is desirable that the camera housing 21 is configured of the blue or green material which is easily noticed inside the body, but similarly, it is more desirable that a film on a surface of the camera side cable 12 is configured of the blue or green material which is easily noticed inside the body. Furthermore, it is also desirable that the camera side cable connector 12a is configured of similarly colored material. In this manner, by making the color inside the body which is red or yellow into the blue or green color that is a complementary color, it is possible to make the visual recognition easy during the installation work or the withdrawing work inside the body, which will be described later. For example, even when the camera unit 11 is incorrectly dropped in the body and is hidden by the shade of the organ, since the camera side cable 12 is longer compared to the camera unit 11, there are more cases where the camera unit 11 is seen at a location which can be visually recognized, and can be immediately found. Accordingly, by coloring the camera side cable 12 in blue and green, a special effect is achieved in which the time of the installation work of the camera unit 11 can be shortened and safety is also improved. In this manner, in coloring the camera side cable 12, it is possible to use a color (a color which is easily seen in the body) that corresponds to visible light having a wavelength of 420 nm to 570 nm (preferably, 450 nm to 530 nm).

As described above, other than coloring with a blue or green material, the phosphorescent material or the reflecting material which is likely to be visually recognized may be used. In this manner, since it is possible to immediately find the camera unit 11, even when the camera unit 11 is in the shade of an organ that is unlikely to be visually recognized, or at an end of a visual field where illumination light is unlikely to reach, the phosphorescent material or the reflecting material is particularly effective.

In FIG. 1, by inserting a pin part of the male-shaped (projected) camera side cable connector 12a into the female-shaped (recessed) instrument side cable connector 16a, that is, by making the connector 12a of the camera side cable 12 and the connector 16a of the instrument side cable 16 fitted to each other, the camera side cable 12 and the instrument side cable 16 become connected to each other. However, a configuration in which the male-shaped connector and the female-shaped connector is reversed, or in which the female-shaped camera side cable connector and the male-shaped instrument side cable connector is fitted to each other, may be employed. In addition, in the female-shaped (recessed) camera side cable connector, since the pin part is not exposed to the outside, similar to the male-shaped connector, staining is unlikely to occur on a terminal unit, even in a case where the connector incorrectly touches the inside of the body. Accordingly, it is desirable that the female-shaped (recessed) connector is used in the camera side cable.

Although will be described later in detail, when the camera unit 11 and the camera support tube 13 are connected to each other, the camera side cable 12 (including the connector 12a) is drawn out toward the outside of the body from the inside of the body through the camera support tube 13. Therefore, an outer diameter of the camera side cable connector 12a is smaller than an outer diameter of the camera support tube 13. In other words, when reducing the outer diameter of the camera side cable connector 12a, it is possible to reduce the outer diameter of the camera support tube 13. Accordingly, a special effect is achieved in which low invasiveness is improved. In other words, it is desirable to make the outer diameter of the camera side cable connector 12a as small as possible. For example, as illustrated in FIG. 1, it is desirable that the outer diameter of the camera side cable connector 12a is equal to or smaller than the outer diameter of the instrument side cable connector 16a, and that the outer diameter (cable diameter) of the camera side cable 12 is smaller than the outer diameter (cable diameter) of the instrument side cable 16.

As will be described later, it is possible to provide a slit which reaches from one end to the other end of the camera support tube. In this case, the camera side cable 12 passes through the inside of the camera support tube via the slit from the side surface of the camera support tube. Accordingly, it becomes easy to make the camera side cable (including the connector) pass through the camera support tube. Because the slit is provided, since it is not necessary for the camera side cable connector 12a to pass through the inside of the camera support tube 13, it is possible to reduce the inner diameter of the camera support tube 13 to be smaller than the dimension of the outer diameter of the camera side cable connector 12a. Due to this, if the thickness of the camera support tube 13 is the same, it is possible to further reduce the outer diameter of the camera support tube 13. Accordingly, a special effect is achieved in which low invasiveness is further improved. In addition, a cooling effect of the camera support tube, such as improvement of ventilation properties in the camera support tube due to the slit, is also achieved.

As will be described later, since the camera side cable 12 (including the camera side cable connector 12a) returns to the inside of the body during the withdrawing of the camera unit 11, it is necessary to maintain the instrument side cable connector 16a which is in contact with the camera side cable 12 and a part having a predetermined length from the instrument side cable connector 16a to be clean, in the instrument side cable 16.

(Camera Support Tube 13)

As illustrated in FIG. 1, the camera support tube 13 is a support tube which supports the camera unit 11 by being joined with the camera unit 11 inside the body in a state where the camera side cable 12 is drawn out toward the outside of the body through the inside of the tube.

From the viewpoint of the joining strength with the camera unit 11, the camera support tube 13 is formed of a hard material. The material of the camera support tube 13 is not particularly limited if the material has rigidity which can obtain the joining strength that can stably support the camera unit 11, and which can fix the camera unit 11 at a desirable position and orientation. For example, stainless steel, ceramics (fine ceramics), or reinforced plastic may be used.

One end part 13a (first end part) of the camera support tube 13 is inserted into the body through a body wall 41, such as an abdominal wall. At this time, one end part 13a of the camera support tube 13 may be directly inserted into the body, or one end part 13a may be inserted into the body by using the cannula 31 inserted into the body wall 41 as illustrated in FIG. 1 and by inserting the camera support tube 13 into the cannula 31.

In a case where the cannula 31 is used, as the camera support tube 13, the long camera support tube 13 having the length in an axial direction longer than the cannula 31 is used so that one end part 13a and the other end part 13b (second end part) are exposed from the cannula 31 in a state where the camera support tube 13 is inserted into the cannula 31, is used. In addition, the camera support tube 13 having a size (thickness) which has a void between an outer wall of the camera support tube 13 and an inner wall of the cannula 31 in a state where the camera support tube 13 is inserted into the cannula 31, is used so that it is possible to rotate the camera support tube 13 around the axis in the cannula 31.

The end part 13a inserted into the body joins with the camera unit 11 by the support tube joining portion 14.

Here, a structure of the camera support tube 13 will be described in detail with reference to FIGS. 3(a) to 3(c).

FIG. 3(a) is a perspective view illustrating an example of the camera support tube 13 according to embodiment. FIG. 3(b) are sectional views illustrating each of the camera support tube 13 illustrated in FIG. 3(a) and the support tube joining portion 14 illustrated in FIG. 2(a). FIG. 3(c) is a sectional view illustrating a joined state of the camera support tube 13 and the support tube joining portion 14 illustrated in FIG. 3(b). In FIG. 3(c), the camera side cable 12 is omitted.

As illustrated in FIG. 3(a), the camera support tube 13 preferably has a cylindrical tube structure. As the camera support tube 13 has a cylindrical shape, it is easy to combine the camera support tube 13 with a general cannula, which is the same cylindrical tube.

One end part 13a (inside the body) of the camera support tube 13 and the camera unit 11 inside the body join with each other by the support tube joining portion 14 (joining portion).

As illustrated in FIGS. 3(a) to 3(c), the camera support tube 13 includes a locking male screw 123 which is screwed (screw-fitted) to the locking female screw 23 provided in the support tube joining portion 14, at the end part 13a on a side which is inserted into the body.

As the locking female screw 23 of the camera support tube 13 is screwed to the locking female screw 23 of the support tube joining portion 14 in this manner, it is possible to join the camera unit 11 and the camera support tube 13 to each other with high mechanical strength.

In addition, as illustrated in FIG. 3(a), it is desirable that a slit 223 is provided on one side surface of the camera support tube 13. An advantage of a case where the slit 223 is provided on the side surface of the camera support tube 13 will be described later.

(Control System 3)

As illustrated in FIG. 1, the control system 3 includes the camera unit control instrument 17 and the display 18 (display apparatus).

The camera unit control instrument 17 displays the image sent from the camera unit 11 on the display 18. In addition, the camera unit control instrument 17 sends the control signal to the camera unit 11. The camera unit control instrument 17 and the display 18 may be integrally configured, and may be separately configured.

(Cannula 31)

FIG. 4(a) is a sectional view illustrating a schematic configuration of the cannula 31 used in the embodiment. FIG. 4(b) is a sectional view illustrating a state where the camera support tube 13 illustrated in FIGS. 3(a) to 3(c) is inserted into the cannula 31 illustrated in FIGS. 3(b) and 3(c). FIG. 4(c) is a sectional view illustrating a joined state of the camera support tube 13 inserted into the cannula 31 and the camera unit 11 illustrated in FIG. 2.

As illustrated in FIG. 4(a), the cannula 31 used in the embodiment is a funnel type tube (tube-line device) which includes a head portion 131 and a leg portion 132, and in which the inner diameter of the head portion 131 is greater than the inner diameter of the leg portion 132.

Therefore, in the cannula 31, an end part 31b (outside the body) on the head portion 131 side is thicker than an end part 31a on the leg portion 132 side (inside the body) which is inserted into the body, and the head portion 131 functions as a stopper when the cannula 31 is inserted into the body wall 41.

Accordingly, the camera support tube 13 does not fall out in the body, and can fix the cannula 31 to the body wall 41.

In addition, the cannula 31 includes a valve (support tube holder) 37, and the valve 37 has a value structure which is pressingly expanded when an external force is applied in an orientation of the narrow end part 31a (inside the body) from the thick end part 31b (outside the body).

Therefore, as illustrated in FIG. 4(b), when camera support tube 13 is inserted into the cannula 31 through the valve 37, the valve 37 is pressingly expanded by the camera support tube 13, and the camera support tube 13 is tightly fastened by a biasing force caused by restoration properties. As a result, the camera support tube 13 is fixed to the cannula 31.

In addition, it is preferable that the cannula 31 has a small diameter for realizing low invasiveness. Specifically, it is preferable that the diameter of the cannula 31 is equal to or smaller than 3 mm.

(Fixing Camera Support Tube 13 to Cannula 31 and Joining Camera Support Tube 13 to Camera Unit 11)

Hereinafter, a manner of inserting the camera support tube 13 into the cannula 31 and joining the camera support tube 13 with the camera unit 11 will be described with reference to FIGS. 4(b) and 4(c).

In a case where the camera unit 11 joins with the camera support tube 13 inside the body, first, as illustrated in FIG. 4(b), in a state of passing through the camera side cable 12 inside the camera support tube 13, one end part 13a of the camera support tube 13 is pushed against the thick end part 31b (outside the body) of the cannula 31, and until the end part 13a of the camera support tube 13 is exposed from the cannula 31, the camera support tube 13 is inserted into the cannula 31. At this time, as the valve 37 is pressingly expanded by the camera support tube 13, and the camera support tube 13 is biased due to the restoration properties, the camera support tube 13 is fixed to the cannula 31. In addition, the other end part 13b (outside the body) of the camera support tube 13 is also exposed from the cannula 31.

Next, as illustrated in FIG. 4(c), using the camera side cable 12 as a guide, by inserting and screwing the locking male screw 123 of the end part 13a inside the body of the camera support tube 13 into the locking female screw 23 of the support tube joining portion 14, the locking male screw 123 is put into the locking female screw 23, and the camera unit 11 and the camera support tube 13 join with each other with high mechanical strength. In addition, the locking male screw 123 and the locking female screw 23 are not limited to a screw shape, and may have any shape in which both are able to be fitted to each other, and instead of the locking female screw 23, it is possible to use a press fit structure which uses an elastic member.

In addition, in a case where the camera support tube 13 and the support tube joining portion 14 are inserted and fitted to each other by using a locking claw or the like instead of the screw shape, it is desirable that the strength by which the camera support tube 13 and the support tube joining portion 14 are fitted to each other is set to be smaller than the adhering strength of an adhering and fixing unit which adheres and fixes the camera side cable 12 and the camera unit 11. This is because there is a concern that the adhering and fixing unit is destroyed and the body wall of a patient is damaged as the camera unit is pulled in an outward direction in relation to the body, if the fitting strength of the camera support tube 13 and the support tube joining portion 14 is greater than the adhering strength of the adhering and fixing portion, since it is necessary to insert the camera support tube 13 while holding, pulling, and supporting the cable, and using the cable as a guide, when inserting the camera support tube 13 into the support tube joining portion 14 of the camera unit 11.

For example, specifically, it is desirable that the strength by which the camera support tube 13 and the support tube joining portion 14 are fitted to each other is equal to or less than 30 N (newton) which is smaller than the adhering strength of the adhesion and fixing portion. Furthermore, it is desirable that the most appropriate range is set to be a range of 3 N to 6 N. If the range is set, a special effect is achieved in which the camera support tube 13 and the support tube joining portion 14 can be fitted to each other without applying an excessively large force during the fitting, and installation can be safely performed without continually applying the excessive force since the feeling that the camera support tube 13 is fitted is transferred to the hand.

In addition, FIG. 4(c) illustrates a state where the camera support tube 13 is pulled up, and the camera unit 11 is brought into contact with the end part 13a inside the body of the cannula 31 after the camera support tube 13 and the camera unit 11 join with each other by the support tube joining portion 14.

The camera support tube 13 is fixed to the cannula 31 to be movable in a direction of the external force by applying the external force to the camera support tube 13, for example, by applying a force to the camera support tube 13 with one hand in a state where a practitioner presses the cannula 31 with the other hand.

In other words, the cannula 31 can move the camera support tube 13 in an upward-and-downward direction or in a rotational direction by applying the external force to the camera support tube 13 in the upward-and-downward direction (axial direction) or in the rotational direction (circumferential direction), and when applying the external force, it is possible to hold (fix) the camera support tube 13 at an arbitrary position of the camera support tube 13 in a height direction or in the rotational direction.

(String-like Member 38)

The string-like member 38 is a fixing tool which fixes the camera support tube 13 in a state where a constant angle is maintained with respect to a body surface 45 by fixing the camera support tube 13 to a fixture (fixed body) fixed to the outside of the body as illustrated in FIG. 1.

A material of the string-like member 38 is not particularly limited if the material having strength which can hold the camera support tube 13 in a state of being fixed to the fixture fixed to the outside of the body, and maintain an angle during the fixing.

In the embodiment, as the fixture fixed to the outside of the body, the trocar 32 (for example, the trocar 32 adjacent to the camera support tube 13) is used.

The trocar 32 is generally a pipe (tube-like member) punctured through an abdomen of the patient for inserting the forceps or the endoscope into the body cavity. As the trocar 32, a general trocar can be used.

In the embodiment, by fixing the camera support tube 13 fixed to the cannula 31 to the trocar 32 by the string-like member 38, the camera support tube 13 is indirectly fixed to the body surface 45.

However, the fixture is not particularly limited if it is possible to attach (fix) a part of the string-like member 38 attached to the camera support tube 13 so as not to bend the string-like member 38 outside the body, so that it is possible to hold the camera support tube 13 at a desirable angle. As the fixture, a fixing device or the like installed on an operating table or an operating room may be employed.

<Method for Installing Camera System for Monitoring inside of Body 1>

Next, both a method for installing an imaging apparatus 2 in the camera system for monitoring the inside of a body 1 according to the embodiment, and a method of use thereof, will be described.

Figure 7:
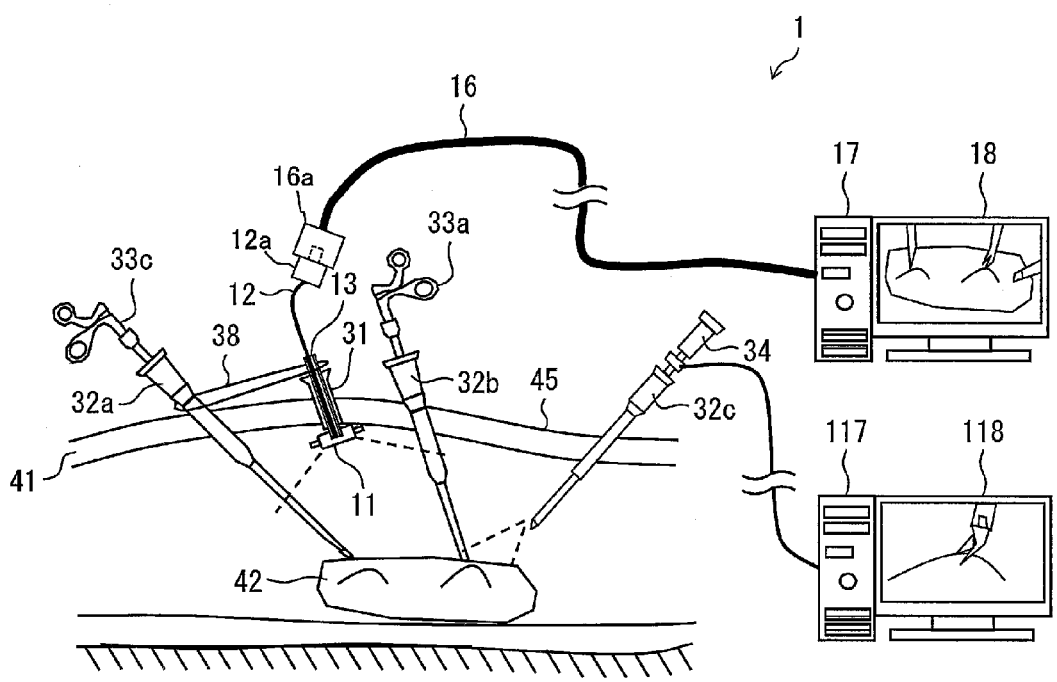
FIG. 7 is a schematic view illustrating a use situation of a camera system for monitoring the inside of a body 1 according to Embodiment 1.

FIGS. 5(a) to 5(h) are schematic views illustrating the method for installing the imaging apparatus 2 in the camera system for monitoring the inside of a body 1 according to Embodiment 1 in order of process. FIGS. 6(a) and 6(b) are perspective views illustrating the process illustrated in FIG. 5(e) in detail. FIG. 6(c) is a plan view illustrating a relationship between the size of the camera side cable connector 12a and the size of the camera support tube 13. FIG. 7 is a schematic view illustrating a use situation of the camera system for monitoring the inside of a body 1 according to the embodiment.

As illustrated in FIG. 5(a), first, the practitioner opens ports 41a to 41c (holes) for inserting the forceps or the endoscope into the body cavity on the body wall 41, and inserts a plurality of trocars 32 (hereinafter, referred to as trocars 32a to 32c) into the ports 41a to 41c.

Furthermore, in order to install the camera unit 11 inside the body cavity, the port 41d is opened at a position where the entire organ including an affected part can be seen on the body wall 41, and the cannula 31 is inserted.

Specifically, by puncturing an obturator in a state where the needle-like obturator (not illustrated) passes through the inside of the cannula 31, the cannula 31 is inserted into the body wall 41.

In addition, after at least one of the trocars 32a to 32c and the cannula 31 is inserted into the body wall 41, the practitioner sends gas into the body through at least one trocar among the trocars 32a to 32c, expands the inside of the body cavity in advance, and ensures a space into which a device is inserted.

Next, as illustrated in FIG. 5(b), the practitioner inserts an endoscope 34 into the body cavity through the trocar 32c, grips the supporting portion 22 by forceps 33a while observing the inside of the body using the endoscope 34, and inserts the imaging apparatus 2 into the body cavity through the trocar 32b.

Next, as illustrated in FIG. 5(c), the practitioner operates the forceps 33a, moves the imaging apparatus 2 to be close to the cannula 31, and inserts forceps 33b into the body cavity through the cannula 31.

Next, as illustrated in FIG. 5(d), the practitioner leads the camera side cable 12 to the outside of the body by pulling out the forceps 33b from the cannula 31 in a state of nipping the camera side cable 12 by the forceps 33b. At this time, the supporting portion 22 in the camera unit 11 becomes gripped by the forceps 33a.

Next, as illustrated in FIG. 5(e), while gripping the supporting portion 22 on both side surfaces of the camera unit 11 by the two forceps 33a and 33c, the practitioner inserts the forceps 33c into the body cavity through the trocar 32a, makes the camera side cable 12 pass through the inside of the camera support tube 13, and inserts the camera support tube 13 into the cannula 31 so that the support tube joining portion 14 of the camera unit 11 and the opening of the cannula 31 become parallel and close to each other.

At this time, in a case where the camera support tube 13 provided with the slit 223 on the side surface is used as the camera support tube 13, as the camera side cable 12 guided toward the outside of the body passes through the inside thereof from the slit 223 on the side surface of the camera support tube 13, the camera support tube 13 is inserted into the cannula 31.

Specifically, as illustrated in FIG. 6(a), first, after pulling up the camera side cable 12 from the cannula 31, a part of the camera side cable 12 is inserted into a lower part of the slit 223 of the camera support tube 13.

Next, the camera support tube 13 is inserted into the cannula 31 as the slit 223 extends along the camera side cable 12. In other words, as illustrated in FIG. 6(b), at the same time when the camera side cable 12 is pulled upward in a state where a part of the camera side cable 12 is inserted into the lower part of the slit 223 of the camera support tube 13, by using the camera side cable 12 as a guide, the camera support tube 13 is inserted into the cannula 31.

In this manner, as the slit 223 is provided on the side surface of the camera support tube 13, when the camera side cable 12 passes through the inside of the camera support tube 13, it is possible to insert the camera side cable 12 into the camera support tube 13 from the slit 223.

Therefore, the camera side cable 12 can easily pass through the inside of the camera support tube 13, and the insertion work of the camera support tube 13 into the body becomes extremely simple.

In addition, in a case where the cannula 31 is used for leading the camera support tube 13 into the body, in a case where the slit 223 is not provided, the length made by adding at least the cannula 31 and the camera support tube 13 is necessary to make the camera side cable 12 drawn out from the cannula 31 pass through the inside of the camera support tube 13.

However, in a case where the slit 223 is provided, the length of the camera side cable 12 may be longer than the length of the cannula 31.

Therefore, as the slit 223 is provided in the camera support tube 13 in this manner, it is possible to reduce the restriction of the length of the camera side cable 12.

In addition, as the slit 223 is provided in the camera support tube 13, as illustrated in FIG. 6(c), the external dimension of the camera side cable connector 12a connected to the camera side cable 12 can be greater than the inner diameter of the camera support tube 13. Therefore, it becomes easy to connect the camera side cable connector 12a to the instrument side cable 16, and it is possible to increase work efficiency. In addition, the external dimension of the camera side cable connector 12a becomes smaller than the inner diameter of the cannula 31.

Next, as illustrated in FIG. 5(f), the practitioner inserts the end part 13a inside the body of the camera support tube 13 exposed from the cannula 31 into the support tube joining portion 14 of the camera unit 11 and screws the end part 13a, by using the camera side cable 12 as a guide. Accordingly, in a state where the camera side cable 12 passes through the inside of the camera support tube 13, the camera support tube 13 and the camera unit 11 join with each other at the support tube joining portion 14 inside the body.

In addition, in a case where the camera support tube 13 and the support tube joining portion 14 are inserted and fitted to each other by using the locking claw or the like instead of the screw shape, when the camera support tube 13 is inserted into the support tube joining portion 14 of the camera unit 11, a force (for example, 3 N to 6 N) necessary for fitting the camera support tube 13 and the support tube joining portion 14 to each other, is sufficiently reduced to be smaller than the adhering strength (for example, equal to or greater than 30 N) of the adhering and fixing unit of the camera side cable 12 and the camera unit 11 when the camera support tube 13 is inserted into the support tube joining portion 14 of the camera unit 11. Therefore, by pulling the cable while using the cable as the guide, it is possible to safely insert the camera support tube 13, and make the camera support tube 13 fitted.

Next, as illustrated in FIG. 5(g), the practitioner pulls up the camera support tube 13 and brings the camera unit 11 into contact with the end part 13a inside the body of the cannula 31, so that the widest area possible inside of the body cavity can be imaged. Since the camera support tube 13 is tightly fastened by the valve 37 (refer to FIGS. 4(a) to 4(c)) of the cannula 31, the camera support tube 13 and the camera unit 11 maintain the fastened state.

Next, the height, the orientation, and the angle in the body cavity of the camera unit 11 is determined by operating the camera support tube 13, and as illustrated in FIG. 5(h), the fixing is performed by the fixing tool, such as the string-like member 38.

The height of the camera unit 11 in the body cavity is determined by gradually lowering the camera support tube 13 or by finely adjusting the camera support tube 13 in the upward-and-downward direction as necessary, from a state where the camera unit 11 is brought into contact with the end part 13a inside the body of the cannula 31 as illustrated in FIG. 5(g).

In addition, the orientation of the camera unit 11 in the body cavity is determined by rotating the camera support tube 13 in the circumferential direction.

The camera support tube 13 can be fixed to the cannula 31 at the arbitrary position by the biasing force of the valve 37, and is indirectly fixed to the body surface 45 via the cannula 31.

In addition, the orientation of the camera unit 11 is determined by inclining the camera support tube 13 using elasticity of the body wall 41.

At this time, by fixing the camera support tube 13 to the trocar 32 which is close to the camera support tube 13, such as the trocar 32a, by the fixing tool, such as the string-like member 38, without supporting the camera support tube 13, the practitioner can maintain the inclination of the camera support tube 13 with respect to the body surface 45.

As illustrated in FIG. 7, after installing the camera unit 11 in the body, the camera side cable 12 and the instrument side cable 16 are joined to each other by using the camera side cable connector 12a.

Accordingly, a local image of a treatment part (surgical site) is displayed on a display 118 by an endoscope control instrument 117 connected to the endoscope 34, and the entire image of the inside of an organ 42 imaged by the camera unit 11 is displayed on the display 18 by the camera unit control instrument 17.

Accordingly, the practitioner can perform treatment by the forceps 33a and the forceps 33c while enlarging and observing the work region (local region) on the display 118, and can ascertain the state (movement of the forceps or the like, a bleeding site, and a residual, such as gauze, outside the work region) outside the work region on the display 18.

<Separation of Camera Unit 11 and Camera Support Tube 13>

Next, a method for separating the camera unit 11 and the camera support tube 13 will be described.

First, the practitioner pulls out the camera support tube 13 from the support tube joining portion 14 of the camera unit 11 by rotating the camera support tube 13 in a direction (that is, a direction in which a screw is loosened) reverse to a direction in which the locking male screw 123 and the locking female screw 23 are screwed to each other, in a state where the supporting portion 22 of the camera unit 11 in the body is gripped by the forceps 33a and the forceps 33c.

In addition, in a case where the camera support tube 13 and the support tube joining portion 14 are inserted and fitted to each other by using the locking claw or the like instead of the screw shape, similar to the time when the camera unit 11 and the camera support tube 13 are separated from each other, it is desirable that the fitting strength of the camera support tube 13 and the support tube joining portion 14 is set to be smaller than the adhering strength of the adhering and fixing unit which adheres and fixes the camera side cable 12 and the camera unit 11. This is because there is a concern that the adhering and fixing unit is destroyed and the body wall of the patient is damaged as the camera unit is pulled in the outward direction in relation to the body, since it is necessary to apply a large force when removing the camera support tube 13 from the camera unit 11 if the fitting strength of the camera support tube 13 and the support tube joining portion 14 is greater than the adhering strength of the adhering and fixing unit.

For example, if the fitting strength is set to be in a range of 3 N to 6 N, a special effect is achieved in which the camera support tube 13 can be removed without applying an excessively large force, and the camera support tube 13 can be safely separated without continually applying the excessive force since the feeling that the camera support tube 13 is removed is transferred to the hand.

Furthermore, after separating the camera support tube 13 and the camera side cable 12 from each other by pulling out the camera support tube 13 from the cannula 31, the practitioner leads the camera unit 11 and the camera side cable 12 to the outside of the body from the trocar 32a or the trocar 32b.

<Effect>

As described above, according to the embodiment, the camera unit 11 and the camera support tube 13 join with each other with high mechanical strength, and the supporting force of the camera unit 11 is higher than that in the related art. In addition, since the camera side cable 12 is guided toward the outside of the body through the inside of the camera support tube 13, after the camera unit 11 and the camera support tube 13 join each other, a load is not applied to the camera side cable 12, the camera side cable 12 is not exposed to the inside of the body, and the camera side cable 12 does not come into contact with the body wall 41. Accordingly, certainty (waterproof and stainproof properties of the connected part) of the electric connection of the camera side cable 12 and the circuit board 19 is increased. Therefore, it is possible to realize the camera system for monitoring the inside of a body 1 having high reliability.

The practitioner can operate the camera support tube 13 and can change the direction of the visual field of the camera unit 11. Specifically, by inclining the camera support tube 13 using elasticity of the body wall 41, it is possible to change the direction of the visual field of the camera unit 11 joined to the camera support tube 13.

Since both the cannula 31 and the camera support tube 13 inserted into the cannula 31 are cylindrical tubes, it is possible to easily rotate the camera support tube 13 around the axis. Accordingly, the practitioner can change the rotational direction of the visual field of the camera unit 11 joined to the camera support tube 13.

The camera support tube 13 can move in a longitudinal direction (an extending direction of the tube) which is the axial direction thereof. Therefore, by pushing the camera support tube 13 to the inside of the body and by pulling up the camera support tube 13 to the outside of the body, the practitioner can change imaging zoom (distance to an object) of the camera unit 11 joined to the camera support tube 13.

As the camera support tube 13 is fixed to the cannula 31, the position and the rotational direction of the camera support tube 13 are maintained.

The camera support tube 13 can be fixed to the fixed body fixed to the outside of the body, such as the trocar 32 (for example, the trocar 32a or the trocar 32b) in the periphery, by using the string-like member 38. Accordingly, it is possible for the camera support tube 13 to be fixed in a desirable state.

In other words, by fixing the camera support tube 13 to the fixed body outside the body, such as the trocar 32, in a state where the camera support tube 13 is inclined by using elasticity of the body wall 41, the practitioner can hold the inclination of the camera support tube 13, even when the practitioner does not support the camera support tube 13.

Therefore, according to the embodiment, it is possible to hold the state of the camera support tube 13, even when the practitioner does not support the camera support tube 13.

Therefore, according to the embodiment, it is possible to arbitrarily set the direction of the visual field in the camera unit 11 and the rotational direction of the visual field, to arbitrarily set the imaging zoom (distance to the object) to be within an allowable range of the length of the camera support tube 13, and to fix the camera support tube 13 at a desirable position. Due to this, it is possible to realize the camera system for monitoring the inside of a body having high usability.

<Modification Example>

(Method for Joining Camera Support Tube 13 and Camera Unit 11 to each Other)

In the embodiment, a case where the camera support tube 13 and the camera unit 11 are screwed to each other as the locking male screw 123 is provided in the camera support tube 13 and the locking female screw 23 is provided in the support tube joining portion 14, will be described as an example.

However, the method for joining the camera support tube 13 and the camera unit 11 to each other is not limited thereto, and any shape in which the camera support tube 13 and the support tube joining portion 14 are able to be fitted to each other may be employed.

Figure 8:
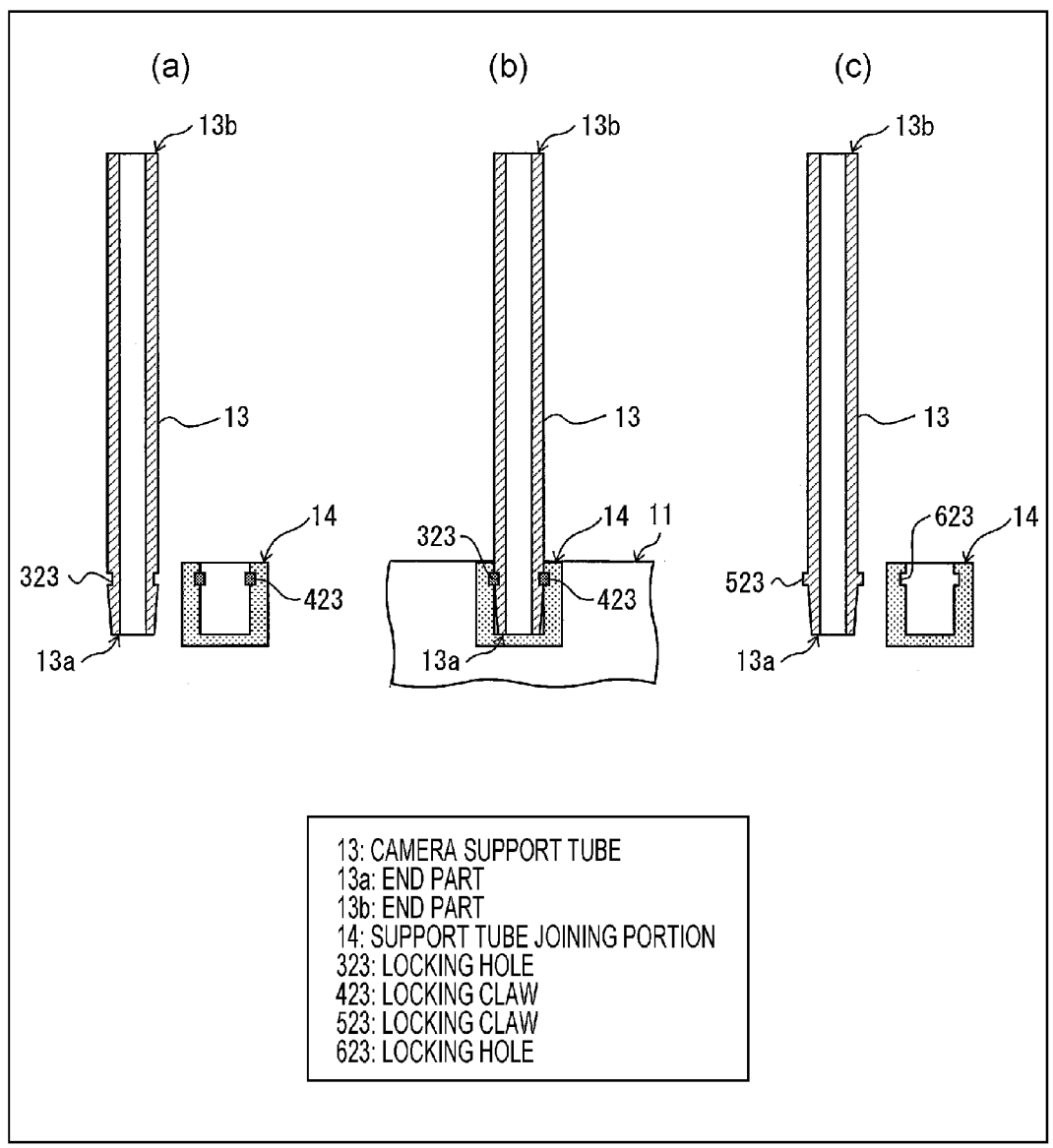
FIGS. 8(a) and 8(b) are respectively sectional views illustrating modification examples of the camera support tube and the support tube joining portion according to Embodiment 1.

FIGS. 8(*a*) to 8(*c*) are respectively sectional views illustrating modification examples of the camera support tube 13 and the support tube joining portion 14 according to the embodiment.

FIGS. 8(*a*) and 8(*b*) illustrate an example in which a locking hole 323 is provided in the camera support tube 13 and a locking claw 423 is provided in the support tube joining portion 14.

FIG. 8(*c*) illustrates an example in which a locking claw 523 is provided in the camera support tube 13 and a locking hole 623 is provided in the support tube joining portion 14.

FIGS. 8(*a*) and 8(*c*) are sectional views illustrating sections of each of the camera support tube 13 and the support tube joining portion 14 in each modification example. FIG. 8(*b*) is a sectional view illustrating a state where the camera support tube 13 illustrated in FIG. 8(*a*) is inserted into the support tube joining portion 14.

As illustrated in FIGS. 8(*a*) and 8(*b*), in the camera support tube 13 according to the modification example, a part further on the front side than the locking hole 323 has a tapered shape. Therefore, the tip end (inside the body) of the camera support tube 13 is not hooked to the locking claw 423 of the support tube joining portion 14, and when pushing the camera support tube 13 until the tip end thereof reaches a deep part of the support tube joining portion 14, the locking hole 323 is fitted to the locking claw 423.

In addition, in FIG. 8(*c*), a case where a part that is further than the locking hole 323 on the front side of the camera support tube 13 has a tapered shape, is illustrated as an example.

However, the camera support tube 13 is not limited to the above-described structure. Both end parts of the camera support tube 13 may have the same thickness.

In the modification examples, in order to separate the camera unit 11 and the camera support tube 13 from each other, it is preferable to design that the engagement of the locking claw 423 and the locking hole 323 or the engagement of the locking claw 523 and the locking hole 623 are released by applying a force which is equal to or greater than a threshold value, for example, implying elasticity to the locking claws 423 and 523, or implying flexibility to the support tube joining portion 14. Otherwise, it is desirable to design that the locking claw 423 retreats (changes to a state of not being protruded) from the wall surface in the opening of the support tube joining portion 14, or the locking claw 523 retreats from the surface of the camera support tube 13, by an external force, such as a magnetic force or electricity.

Instead of joining the camera support tube 13 and the support tube joining portion 14 to each other by using the locking male screw 123 and the locking female screw 23, or by using the locking claws 423 and 523 and the locking holes 323 and 623 as described above, it is also possible to join the camera support tube 13 and the support tube joining portion 14 to each other by forming the inner wall of the support tube joining portion 14 with the elastic material, such as rubber, and by pressing the camera support tube 13 to the support tube joining portion 14.

In this manner, in a case where the camera support tube 13 and the support tube joining portion 14 are inserted and fitted to each other by using the above-described locking claw instead of the screw shape, it is desirable that the strength by which the camera support tube 13 and the support tube joining portion 14 are fitted to each other is set to be smaller than the adhering strength (for example, equal to or greater than 30 N) of the adhering and fixing unit of the camera side cable 12 and the camera unit 11. This is because there is a concern that the adhering and fixing unit is destroyed and the body wall of the patient is damaged as the camera unit is pulled in the outward direction in relation to the body, if the fitting strength of the camera support tube 13 and the support tube joining portion 14 is greater than the adhering strength of the adhering and fixing portion, since it is necessary to insert the camera support tube 13 while holding, pulling, and supporting the cable, and using the cable as a guide, when inserting the camera support tube 13 into the support tube joining portion 14 of the camera unit 11.

For example, specifically, it is desirable that the strength by which the camera support tube 13 and the support tube joining portion 14 are fitted to each other is equal to or less than 30 N (newton) which is smaller than the adhering strength of the adhesion and fixing unit. Furthermore, it is desirable that the most appropriate range is set to be a range of 3 N to 6 N. If the range is set, a special effect is achieved in which the camera support tube 13 and the support tube joining portion 14 can be fitted to each other without applying an excessively large force during the fitting, and installation can be safely performed without continually applying the excessive force since the feeling that the camera support tube 13 is fitted is transferred to the hand.

In addition, in case of the above-described fitting strength, since the camera support tube 13 and the support tube joining portion 14 sufficiently come into contact with each other, when the side surfaces of the camera support tube 13 and the support tube joining portion 14 are formed of a material having excellent thermal conductive properties, it is possible to improve heat radiation properties of the camera unit 11.

(Method for Fixing Camera Support Tube 13 to Cannula 31)

Figure 4:
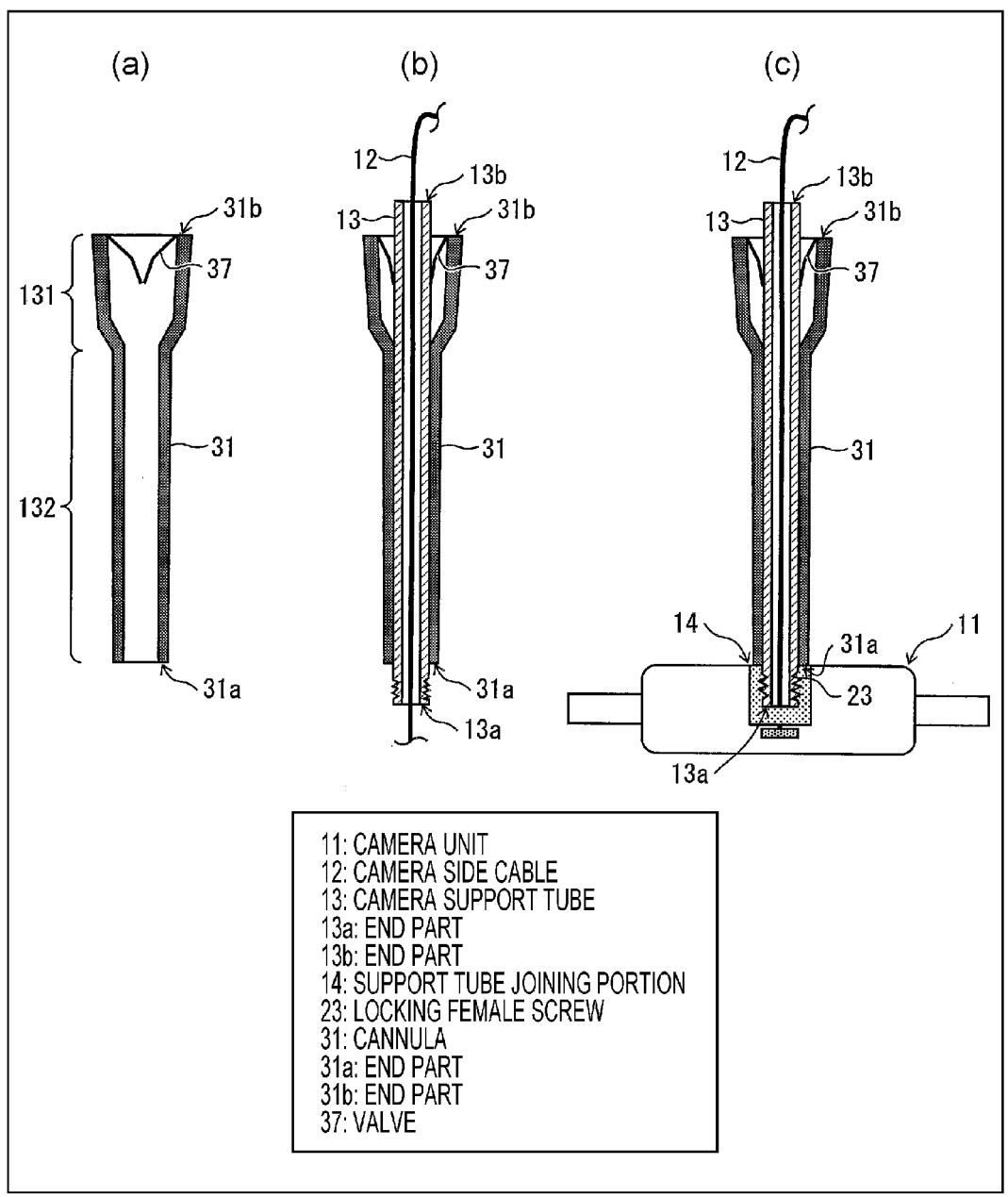
FIG. 4(a) is a sectional view illustrating a schematic configuration of a cannula.
FIG. 4(b) is a sectional view illustrating a state where the camera support tube illustrated in FIGS. 3(a) to 3(c) is inserted into the cannula illustrated in FIGS. 3(b) and 3(c).
FIG. 4(c) is a sectional view illustrating a joined state of the camera support tube inserted into the cannula and a camera unit illustrated in FIG. 2.

In the embodiment, mainly, as illustrated in FIGS. 4(*a*) to 4(*c*), a case where the camera support tube 13 is fixed to the cannula 31 by the valve 37 in the cannula 31 is described as an example. However, the embodiment is not limited thereto.

Figure 9:
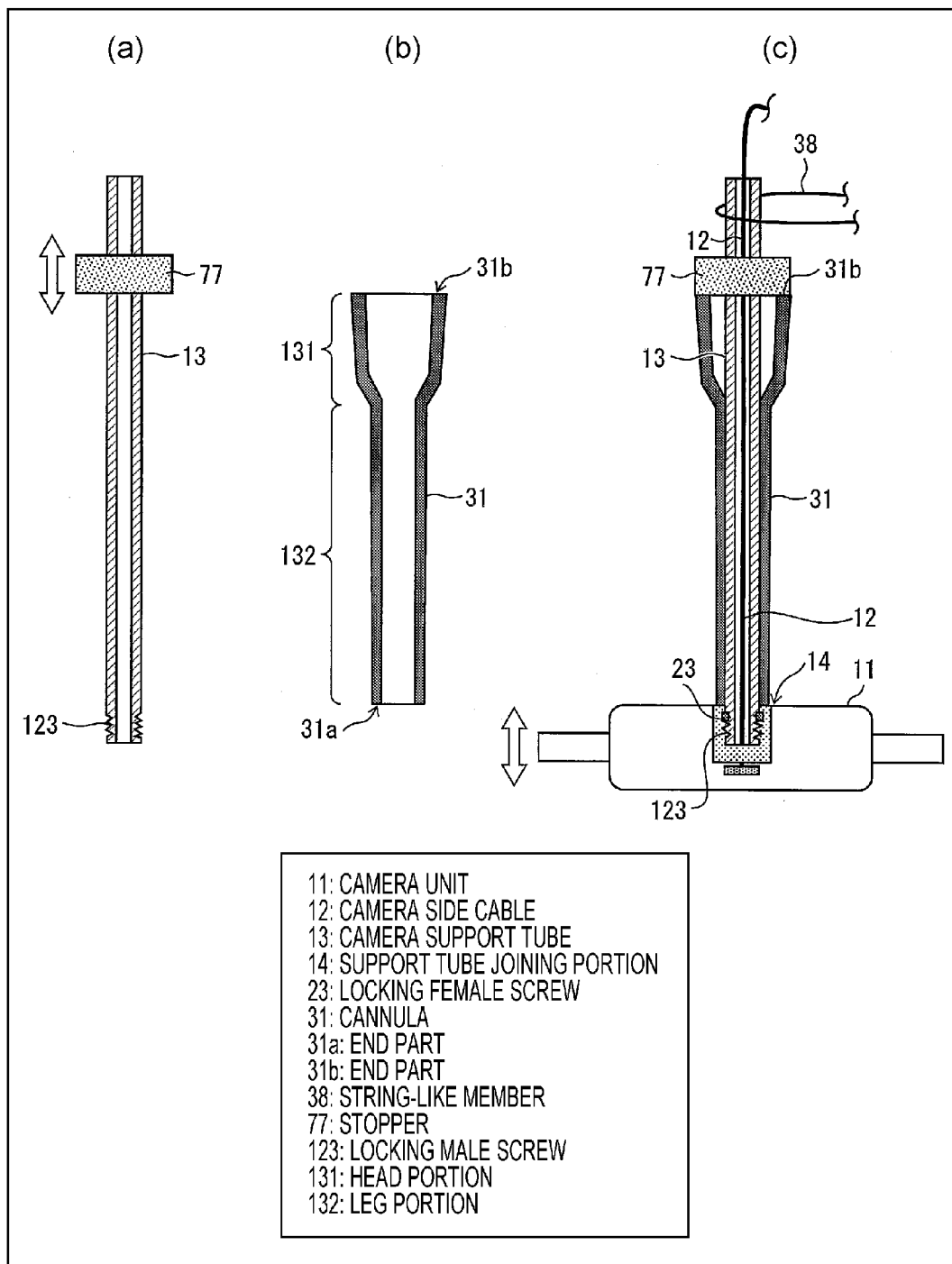
FIG. 9(a) is a sectional view illustrating a schematic configuration of the camera support tube according to the modification example of Embodiment 1 combining with a stopper provided in the camera support tube.
FIG. 9(b) is a sectional view illustrating a schematic configuration of a cannula according to a modification example of Embodiment 1.
FIG. 9(c) is a sectional view illustrating a joined state of the camera support tube illustrated in FIG. 9(a), which is inserted into the cannula illustrated in FIG. 9(b), and the imaging apparatus.

FIG. 9(*a*) is a sectional view illustrating a schematic configuration of the camera support tube 13 according to the modification example combining with a stopper 77 provided in the camera support tube 13. FIG. 9(*b*) is a sectional view illustrating a schematic configuration of the cannula. FIG. 9(*c*) is a sectional view illustrating a joined state of the camera support tube 13 illustrated in FIG. 9(a) which is inserted into the cannula 31 illustrated in FIG. 9(b), and the imaging apparatus 2.

In the modification example, as illustrated in FIGS. 9(a) and 9(c), a case where the locking female screw 23 is provided in the camera support tube 13 and the locking female screw 23 is provided in the support tube joining portion 14 is illustrated as an example.

However, it is needless to say that the camera support tube 13 and the support tube joining portion 14 are not limited thereto, and the camera support tube 13 and the support tube joining portion 14 illustrated in FIGS. 8(a) and 8(b) or in FIG. 8(c), may be used.

As illustrated in FIG. 9(b), the cannula 31 according to the modification example has a configuration similar to that of the cannula 31 illustrated in FIG. 4(a), except that the valve 37 is not provided on the inside thereof.

In the modification example, as the cannula 31, a general cannula 31 on the market can be used.

In the modification example, instead of providing the valve 37 on the inside of the cannula 31, as illustrated in FIGS. 9(a) and 9(c), the stopper 77 (support tube holder) which can move along the axial direction (extending direction) of the camera support tube 13 is mounted on the camera support tube 13.

The stopper 77 is an elastic body, such as rubber, which is inserted into a camera support tube 81, and can be moved by the operation of the practitioner. In addition, since the stopper 77 and the camera support tube 13 have a screw structure, it is also possible to make the stopper 77 movable.

As the stopper 77 is mounted on the camera support tube 13 in this manner, when the camera support tube 13 is inserted into the cannula 31, the stopper 77 abuts against an edge (outside the body) of the cannula 31, and the camera support tube 13 is held by the cannula 31. Furthermore, as the locking hole 323 of the camera support tube 13 is fitted to the locking claw 423 of the camera unit 11, the camera unit 11 and the camera support tube 13 join with each other with high mechanical strength. In addition, by moving the stopper 77 up and down, the practitioner can change the position (imaging zoom) of the camera unit 11 in the body, and to change the orientation of the camera unit 11 by rotating the camera support tube 13.

In addition, in a case where the camera support tube 13 and the support tube joining portion 14 are inserted and fitted to each other by using the locking claw, it is necessary that holding strength of the stopper 77 which holds the camera support tube 13 by the cannula 31 is greater than the fitting strength of the camera support tube 13 so that the camera support tube 13 is not removed from the support tube joining portion 14 provided in the camera unit 11. Specifically, for example, in a case where the fitting strength of the inserted camera support tube 13 is within a range of 3 N to 6 N, strength which is greater than the range, or strength which is equal to or greater than at least 5 N, is necessary. In addition, since it is not necessary that the fitting strength is equal to or greater than the strength of the cable, it is desirable that the most appropriate range is from 5 N to 50 N.

As illustrated in FIG. 9(c), the camera system for monitoring the inside of a body 1 according to the modification example includes the cannula 31 (holding tube), the stopper 77, and the string-like member 38, which are illustrated in FIGS. 9(a) to 9(c).

Therefore, in the modification example, by fixing the camera support tube 13 to the fixed body, such as the trocar 32, which is fixed to the outside of the body using the string-like member 38, it is also possible to fix the camera support tube 13 in a state where a constant angle is maintained with respect to the body surface 45.

(Slit 223)

Figure 3:
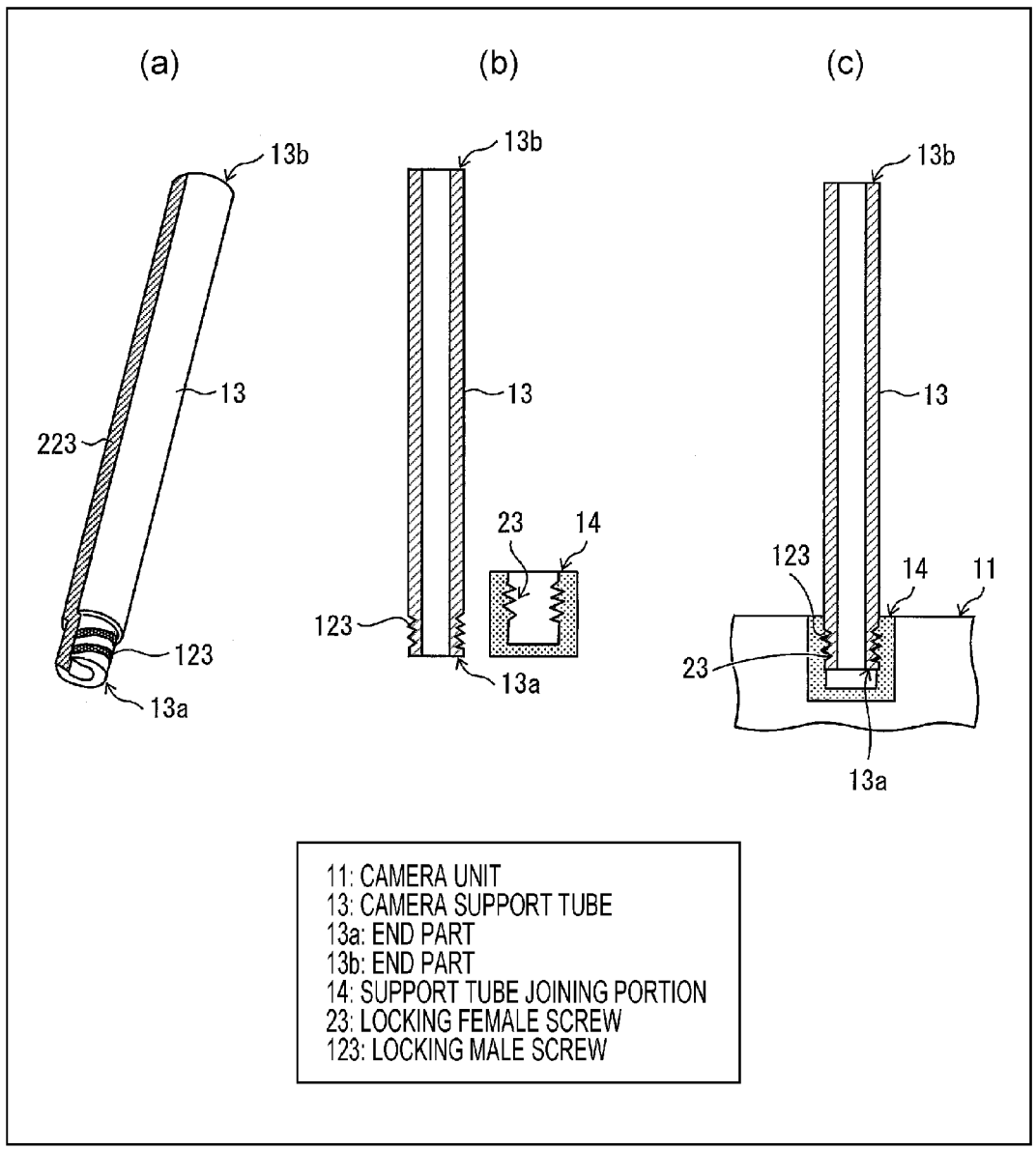
FIG. 3(a) is a perspective view illustrating an example of a camera support tube according to Embodiment 1.
FIG. 3(b) is a sectional view illustrating sections of each of the camera support tube illustrated in FIG. 3(a) and a support tube joining portion illustrated in FIG. 2(a).
FIG. 3(c) is a sectional view illustrating a joined state of the camera support tube and the support tube joining portion which are illustrated in FIG. 2(b).

In FIGS. 3 and 6(a) and 6(b), a case where the slit 223 on the side surface of the camera support tube 13 has a linear shape is illustrated as an example, but the shape of the slit 223 is not limited thereto.

For example, the camera support tube 13 may be configured of a crank type slit 223 in which a lower slit cut upward in the longitudinal direction (axial direction of the camera support tube 13) from one opening (inside the body) of the camera support tube 13, and an upper slit cut downward in the longitudinal direction from the other opening (outside the body) at a position deviated by 90 degrees from the lower slit, are linked to a cylindrical tube by a slit in a lateral direction.

Otherwise, the camera support tube 13 may be configured of a spiral type slit 223 in which the lower slit and the upper slit are linked by a curved slit (a slit in a diagonal direction may be employed).

Similar to the crank type or the spiral type, in a case where a part of the slit 223 is oriented in a direction different from the axial direction (longitudinal direction) of the camera support tube 13, the camera support tube 13 is rotated by approximately 90 degrees in a state where a part of the camera side cable 12 passes through the lower slit of the camera support tube 13, and furthermore, the camera support tube 13 is inserted into the cannula 31 so that the upper slit goes along the camera side cable 12.

Accordingly, the camera side cable 12 inserted from the slit 223 is not removed from the camera support tube 13, the work of the practitioner becomes even easier, and the work becomes easy.

(Fixing by String-like Member 38)

In the embodiment, a case where the camera support tube 13 is fixed to the fixed body, such as the trocar 32, by attaching the string-like member 38 to the end part 13b outside the body of the camera support tube 13, is described as an example. However, the embodiment is not limited thereto, and the camera support tube 13 may be fixed by attaching the string-like member 38 to the cannula 31 to which the camera support tube 13 is fixed, and by fixing the cannula 31 to the fixed body.

[Embodiment 2]

Another embodiment of the present invention will be described based on FIGS. 10 to 13 as follows. In addition, in the embodiment, differences from Embodiment 1 will be mainly described, configuration elements having the same function as those of the configuration elements used in Embodiment 1 will be given the same reference numerals, and the description thereof will be omitted. In addition, in the embodiment, it is also needless to say that modifications similar to those of Embodiment 1 are possible.

In Embodiment 1, a case where the string-like member 38 is used as the fixing tool which fixes the camera support tube 13 inserted into the cannula 31 to the outside of the body, is described as an example, but the fixing tool and the method for fixing the camera support tube 13 are not limited thereto.

In the embodiment, another example of the fixing tool and the method for fixing the camera support tube 13 will be described.

FIGS. 10 to 13 are respectively perspective views illustrating an example of a schematic configuration of main parts of the camera system for monitoring the inside of a body 1 according to the embodiment. FIGS. 10 to 13 respectively illustrate an example of the support tube fixing member.

<Example 1 of Fixing Tool>

Figure 10:
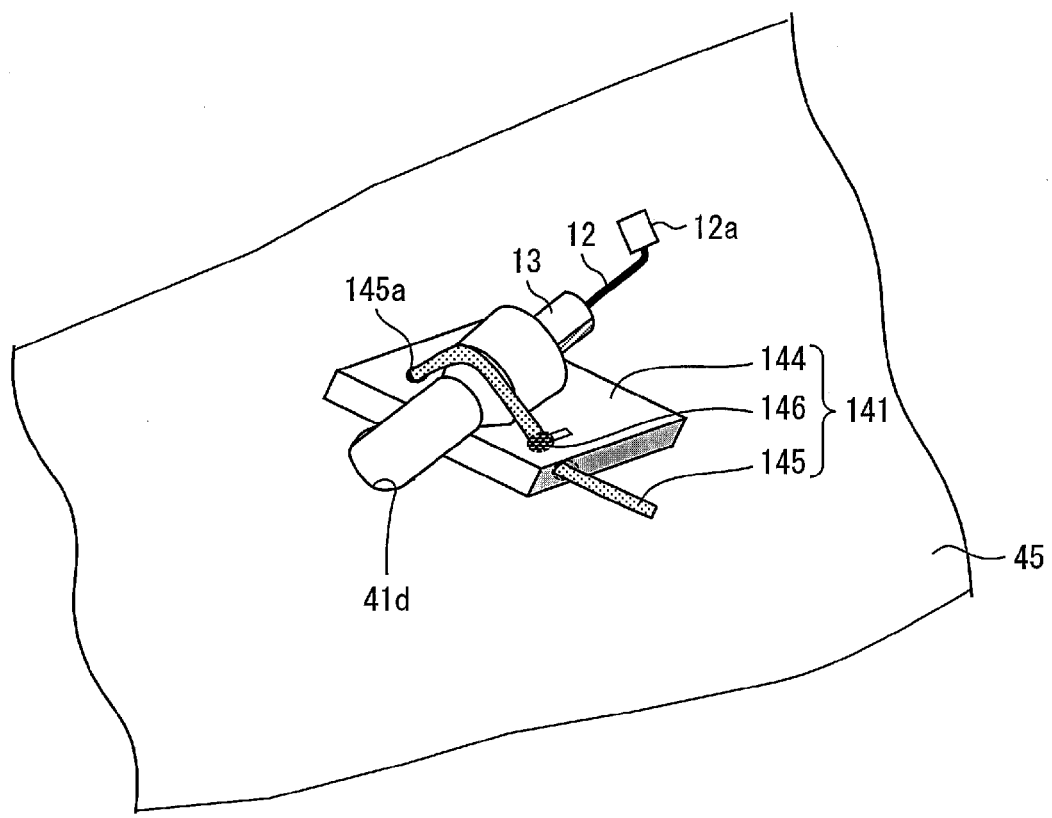
FIG. 10 is a perspective view illustrating an example of a schematic configuration of main parts of a camera system for monitoring the inside of a body according to Embodiment 2.

As illustrated in FIG. 10, the camera system for monitoring the inside of a body 1 according to the example includes the cannula 31 illustrated in FIGS. 4(a) to 4(c), and a fixing device 141 (dedicated device, fixing tool).

In the example, as the fixing tool, instead of the string-like member 38, by using the dedicated fixing device 141 which can directly fix the camera support tube 13 to the body surface 45, the camera support tube 13 which is fixed to the cannula 31 is fixed.

The fixing device 141 according to the example includes a support table 144 provided with an adhesive layer, which is not illustrated, on one surface (contact surface with the body surface 45); an accessory band 145 (belt-like string) which is fixed to a surface opposite to the adhesive layer in the support table 144; and an adjuster 146 which adjusts the fixing length of the band 145. In addition, in order to increase adhesiveness with the body surface 45, it is desirable that a surface member which configures the contact surface with the body surface 45 uses a flexible member that can make the body surface 45 adhered in a rounded shape. In this manner, it is possible to set a range of the most appropriate holding strength, which will be described later.

In the band 145, while one end part is directly fixed to the support table 144, the other end part is fixed to the support table 144 via the adjuster 146. The fixing length of the band 145 can be arbitrarily adjusted by adjusting the length from a fixing end 145a of the band 145 which is directly fixed to the support table 144, to the adjuster 146 which fixes the other end part of the band 145 that is a free end to the support table 144.

In the example, by fixing the cannula 31 to which the camera support tube 13 is fixed, to the support table 144 by the band 145, in a state where the fixing device 141 is fixed to the body surface 45 by the adhesive layer, the camera support tube 13 is fixed to the body surface 45 via the cannula 31.

Therefore, in the example, similar to Embodiment 1, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, by adjusting the fixing position of the cannula 31 by the band 145, it is possible to change the fixing angle (inclination) of the cannula 31 and the camera support tube 13 with respect to the body surface 45. Accordingly, in the embodiment, it is also possible to fix the cannula 31 and the camera support tube 13 at a desirable angle, and to arbitrarily change the direction of the visual field of the camera unit 11.

Accordingly, in the example, it is possible for the camera support tube 13 to be fixed in a desirable state.

In the example, the adjuster 146 is used in adjusting the fixing length of the band 145 as illustrated in FIG. 10, but a method for adjusting the fixing length of the band 145 is not limited thereto. For example, instead of using the adjuster 146, as the band 145, a band provided with a surface fastener, such as a magic tape (registered trademark), may be used.

In the example illustrated in FIG. 10, a case where the cannula 31 is tied to the support table 144 by fastening (pressing) the cannula 31 with the band 145, is described, but the camera support tube 13 may be tied to the support table 144 by fastening (pressing) the camera support tube 13 by the band 145.

In a case where the camera support tube 13 is fastened by the band 145, the camera support tube 13 may be fixed at a desirable position by fastening the support tube 13 with the band 145 again after adjusting the fixing length of the band 145, loosening the band 145, moving the support tube 13 or the support table 144, and adjusting the position of the support tube 13. Otherwise, by adjusting the fixing length of the band 145, giving the band 145 elasticity, and adjusting fastening strength, the support tube 13 may be fixed so that the support tube 13 can be moved as a force which is equal to or greater than a certain level is applied to the support tube 13.

In the example, as described above, a case where the cannula 31 illustrated in FIGS. 4(a) to 4(c) is used as the cannula 31, is described as an example. However, in a case where the camera support tube 13 is fastened by the band 145, since the movement of the camera support tube 13 is further restricted by the band 145, the camera support tube 13 is not necessarily fixed to the cannula, and a general cannula can be used as the cannula.

In addition, in order to prevent the camera support tube 13 from being removed from the support tube joining portion 14 provided in the camera unit 11, it is necessary to increase not only the cable holding strength of a cable fastener 43 (cable holder) which holds the camera side cable 12 in the camera support tube 13, but also the holding strength of all of the fixing members for supporting the camera support tube 13, such as holding strength of the valve 37 or the stopper 77 which holds the camera support tube 13 in the cannula 31, holding strength of the band 145 or a surface fastener which holds the camera support tube 13 or the cannula 31 in the support table 144, or adhering strength of the adhesive layer which fixes the support table 144 to the body surface 45, to be greater than the fitting strength of the camera support tube 13. Specifically, for example, in a case where the fitting strength of the inserted camera support tube 13 is from 3 N to 6 N, strength which is greater than the range, that is, strength which is equal to or greater than at least 5 N, is necessary. In addition, since it is not necessary that the strength is equal to or greater than the strength of the cable, it is desirable that the most appropriate range of the holding strength is from 5 N to 50 N. The most appropriate range is similar to that in another example of the support tube fixing member, which will be described later.

According to the above-described holding strength, since the camera support tube 13 and the support tube joining portion 14 sufficiently come into contact with each other, when the side surfaces of the camera support tube 13 and the support tube joining portion 14 are formed of a material having high thermal conductive properties, it is possible to improve heat radiation properties of the camera unit 11.

<Example 2 of Fixing Tool>

Figure 11:
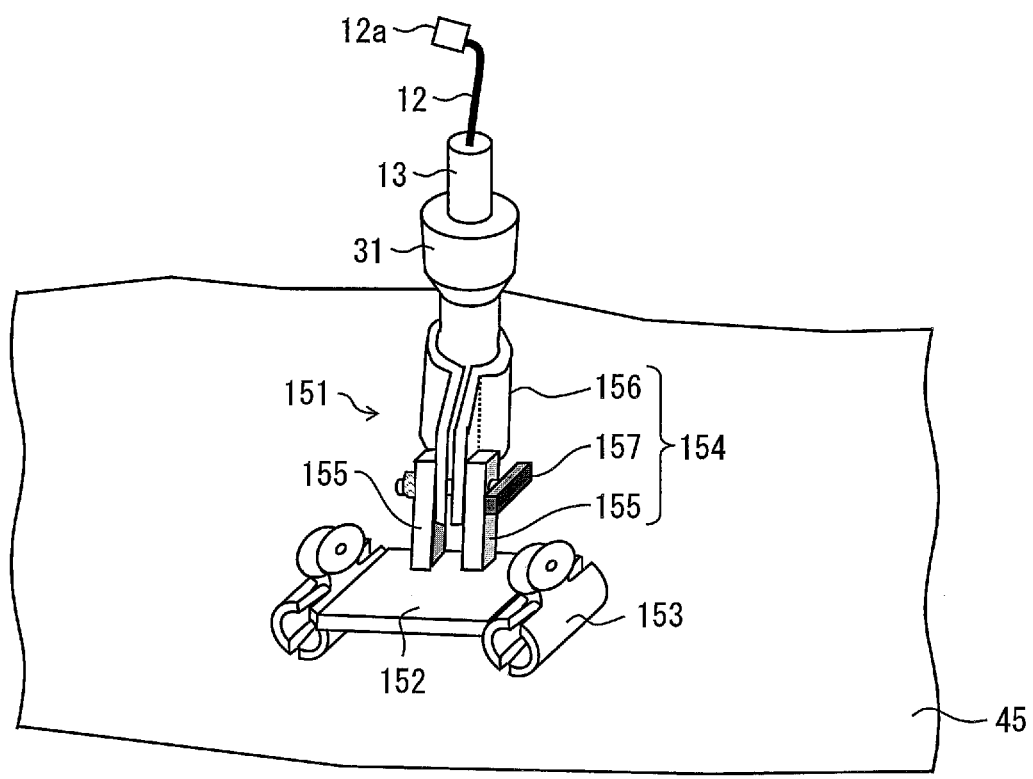
FIG. 11 is a perspective view illustrating another example of the schematic configuration of the main parts of the camera system for monitoring the inside of a body according to Embodiment 2.

As illustrated in FIG. 11, the camera system for monitoring the inside of a body 1 according to the example includes the cannula 31 illustrated in FIGS. 4(a) to 4(c), and a fixing device 151 (dedicated device, fixing tool).

In the embodiment, as the fixing tool, instead of the string-like member 38, by using the dedicated fixing device 151 which can directly fix the camera support tube 13 to the body surface 45, the camera support tube 13 which is fixed to the cannula 31 is fixed. In addition, in the embodiment, the camera support tube 13 is also indirectly fixed to the body surface 45 via the cannula 31.

The fixing device 151 according to the example includes a support table 152, a clip portion 153 (clip-like member) which is made of a pinching member having a clip structure, and a support tube mounting unit 154 provided on a surface side opposite to the body surface 45 on the support table 152.

The fixing device 151 can be directly fixed to the body surface 45 by nipping the skin with the clip portion 153 having a biasing force.

The support tube mounting unit 154 includes arm portions 155 and 155 which are fixed to the support table 152; a clamp portion 156 which is a gripping unit that directly or indirectly grips the camera support tube 13; and a screw fastening handle 157 which fixes the clamp portion 156 by screw-fastening the clamp portion 156 between the arm portions 155 and 155 in a state of gripping the cannula 31 with the clamp portion 156.

In the example, by fixing the cannula 31 to which the camera support tube 13 is fixed to the support table 152 using the clamp portion 156 in a state where the fixing device 151 is fixed to the body surface 45 by the clip portion 153, the camera support tube 13 is fixed to the body surface 45 via the cannula 31.

At this time, by mounting the cannula 31 to which the camera support tube 13 is fixed on the clamp portion 156, turning the screw fastening handle 157, and fastening the cannula 31 by the clamp portion 156, it is possible for the cannula 31 and the camera support tube 13 to be fixed in a desirable state.

Therefore, in the example, similar to Embodiment 1, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, by adjusting the fixing angle of the clamp portion 156 with respect to the art portion 155 and adjusting the fixing angle (inclination) of the cannula 31 and the camera support tube 13 with respect to the body surface 45, it is possible to change the direction of the visual field of the camera unit 11.

Accordingly, in the example, it is also possible for the camera support tube 13 to be fixed in a desirable state.

In addition, in the example illustrated in FIG. 11, a case where the cannula 31 is held by the clamp portion 156 is illustrated as an example, but the camera support tube 13 may be held by the clamp portion 156.

In a case where the camera support tube 13 is held by the clamp portion 156, in a case where the position or the orientation of the camera support tube 13 fixed to the clamp portion 156 is adjusted, after moving the camera support tube 13 by turning the screw fastening handle 157 and loosening the clamp portion 156, and adjusting the position of the camera support tube 13, the camera support tube 13 may be fixed at a desirable position by turning the screw fastening handle 157 and fastening the camera support tube 13 by the clamp portion 156 again. Otherwise, by fastening the fixing strength by the screw fastening handle 157, the camera support tube 13 may be fixed to the clamp portion 156 so that the camera support tube 13 can be moved as a force which is equal to or greater than a certain level is applied to the camera support tube 13.

In the example, as described above, a case where the cannula 31 illustrated in FIGS. 4(a) to 4(c) is used as the cannula 31, is described as an example. However, in a case where the camera support tube 13 is fastened by the clamp portion 156, since the movement of the camera support tube 13 is further restricted by the clamp portion 156, the camera support tube 13 is not necessarily fixed to the cannula, and a general cannula can be used as the cannula.

Instead of the screw fastening handle 157, the clamp portion 156 may adjust the fastening using the biasing force by a spring or the like. In this case, it is desirable that an angle adjustment mechanism which adjusts the fixing angle of the clamp portion 156 is provided in the support tube mounting unit 154. Instead of providing the angle adjustment mechanism in the support tube mounting unit 154, by changing a fixing position of the fixing device 151 by the clip portion 153, the inclination of the camera support tube 13 with respect to the body surface 45 may be adjusted.

In FIG. 11, a case where two clip portions 153 are provided to nip the support table 152 on a side surface of the support table 152, is illustrated as an example, but the method for fixing the support table 152 to the body surface 45 is not limited thereto. For example, one large clip portion which has a biasing force and can nip a part (for example, arm, leg, or abdomen) of the body which is close to the affected part of the patient may be provided on a surface opposite to the art portion 155, which is a lower surface of the support table 152.

<Example 3 of Fixing Tool>

Figure 12:
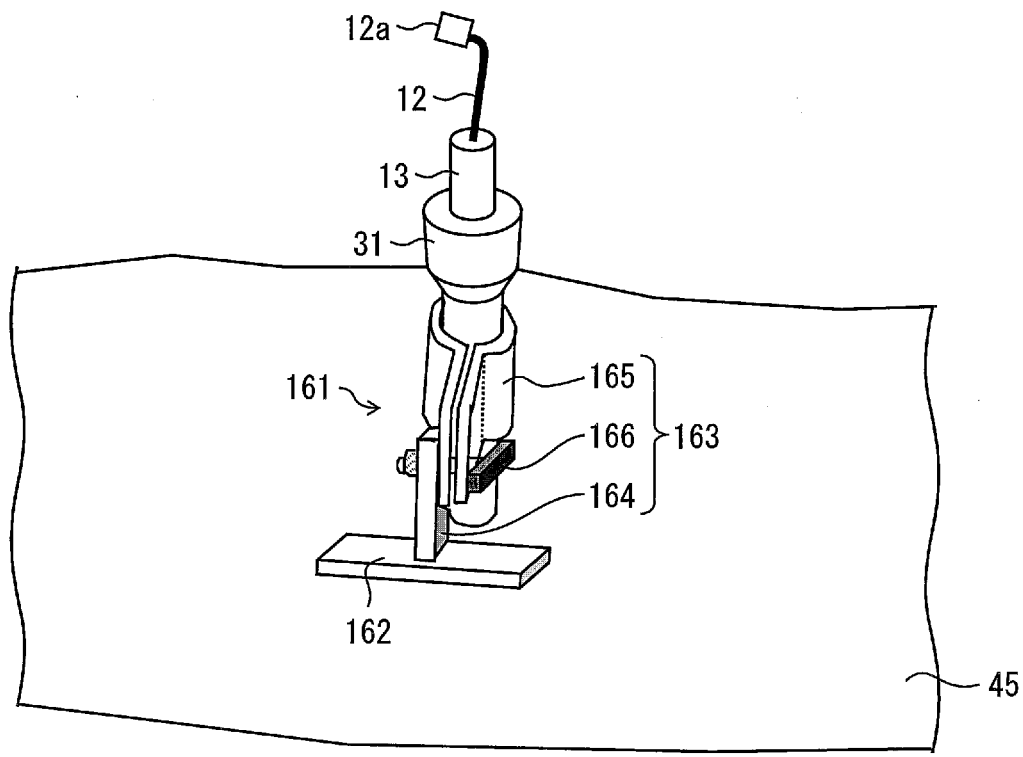
FIG. 12 is a perspective view illustrating still another example of the schematic configuration of the main parts of the camera system for monitoring the inside of a body according to Embodiment 2.

As illustrated in FIG. 12, the camera system for monitoring the inside of a body 1 according to the example includes the cannula 31 illustrated in FIGS. 4(a) to 4(c), and a fixing device 161 (dedicated device, fixing tool).

In the embodiment, as the fixing tool, instead of the string-like member 38, by using the dedicated fixing device 161 which can directly fix the camera support tube 13 to the body surface 45, the camera support tube 13 which is fixed to the cannula 31 is fixed. In addition, in the example, the camera support tube 13 is also indirectly fixed to the body surface 45 via the cannula 31.

The fixing device 161 according to the example includes a support table 162 provided with an adhesive layer, which is not illustrated, on one surface (contact surface with the body surface 45), and a support tube mounting unit 163 provided on a surface side opposite to the body surface 45 on the support table 162. In addition, in order to increase adhesiveness with the body surface 45, it is desirable that a surface member which configures the contact surface with the body surface 45 uses a flexible member that can make the body surface 45 adhered in a rounded shape. In this manner, it is possible to set a range of the most appropriate holding strength, which will be described later.

The support tube mounting unit 163 includes an art portion 164 which is fixed to the support table 162; a clamp portion 165 which is a gripping unit that directly or indirectly grips the camera support tube 13; and a screw fastening handle 166 which fixes the clamp portion 165 by screw-fastening the art portion 164.

In the example, by fixing the cannula 31 to which the camera support tube 13 is fixed to the support table 162 using the clamp portion 165 in a state where the fixing device 161 is fixed to the body surface 45 by the adhesive layer, the camera support tube 13 is fixed to the body surface 45 via the cannula 31.

In the example, similar to the example 2 of the support tube fixing member, by mounting the cannula 31 to which the camera support tube 13 is fixed on the clamp portion 165, turning the screw fastening handle 166, and fastening the cannula 31 by the clamp portion 165, it is also possible for the cannula 31 and the camera support tube 13 to be fixed in a desirable state.

Therefore, in the example, effects similar to those of Example 2 of the support tube fixing member can also be achieved. In addition, in the example, modifications similar to those of the Example 2 of the support tube fixing member are possible.

<Example 4 of Fixing Tool>

Figure 13:
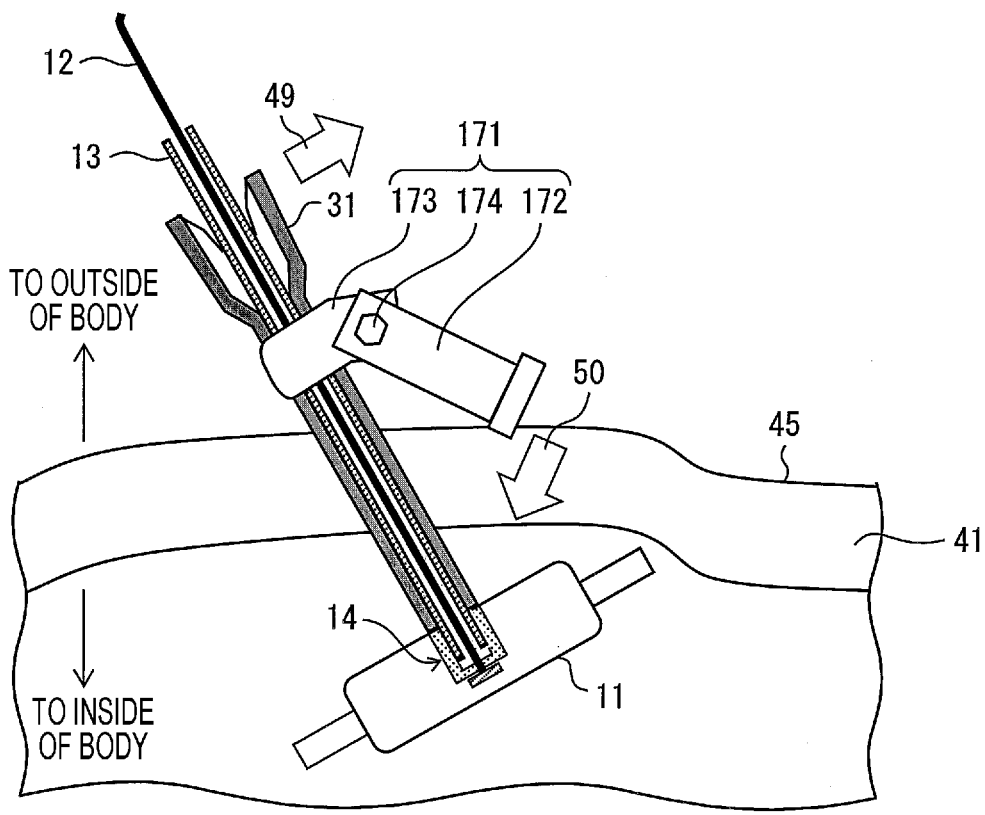
FIG. 13 is a perspective view illustrating further still another example of the schematic configuration of the main parts of the camera system for monitoring the inside of a body according to Embodiment 2.

As illustrated in FIG. 13, the camera system for monitoring the inside of a body 1 according to the example includes the cannula 31 illustrated in FIGS. 4(a) to 4(c), and a fixing device 171 (dedicated device, fixing tool), as the support tube fixing member.

In the embodiment, as the fixing tool, instead of the string-like member 38, by using the dedicated fixing device 171 which can directly fix the camera support tube 13 to the body surface 45, the camera support tube 13 which is fixed to the cannula 31 is also fixed. In addition, in the embodiment, the camera support tube 13 is also indirectly fixed to the body surface 45 via the cannula 31.

The fixing device 171 according to the example includes an art portion 172, a clamp portion 173 which is a gripping unit that directly or indirectly grips the camera support tube 13; and a linking portion 174 which fixes (links) the clamp portion 173 to the art portion 172.

In addition, in the linking portion 174, the screw fastening handle which is not illustrated may be provided. Otherwise, the angle adjustment mechanism which is not illustrated and adjusts the angle made by the art portion 172 and the clamp portion 173 may be provided. In addition, the clamp portion 173 may hold the cannula 31 by screw-fastening, and may hold the cannula 31 using the biasing force by the spring or the like.

The clamp portion 173 and the art portion 172 are linked to each other by the linking portion 174 so that the angle made by the clamp portion 173 and the art portion 172 is an obtuse angle.

The fixing device 171 illustrated in FIG. 13 receives a restoring force 49 generated by elasticity of the body wall 41 when inclining the angle of the camera support tube 13 or the cannula 31 at a contact end part between the camera support tube 13 and the cannula 31 in the clamp portion 173, which is one end part, and uses the restoring force 49 as a force (body wall pressing force 50) which presses the body wall 41 which is the fixed body at a contact end part which is the other end part of the body wall 41 in the art portion 172. Accordingly, it is possible to fix the camera support tube 13 or the cannula 31 at a desirable state.

Therefore, in the example, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In addition, by adjusting the fixing angle of the clamp portion 173 with respect to the art portion 172 and adjusting the fixing angle (inclination) of the cannula 31 and the camera support tube 13 with respect to the body surface 45, it is possible to change the direction of the visual field of the camera unit 11.

In addition, in the example illustrated in FIG. 13, a case where the cannula 31 is held by the clamp portion 173 is illustrated as an example, but in the example, the camera support tube 13 may be held by the clamp portion 173.

In addition, in the example, in a case where the camera support tube 13 is fixed by the clamp portion 173, since the movement of the camera support tube 13 is further restricted by the clamp portion 173, it is also not necessary that the camera support tube 13 is fixed to the cannula, and a general cannula can be used as the cannula.

In addition, in Example 3 of the support tube fixing member, a case where the fixing device 161 is fixed to the body surface 45 by using the adhesive layer is described as an example, but in the fixing device 161 illustrated in FIG. 12, similar to the example, by adjusting the fixing angle of the clamp portion 165 with respect to the art portion 164, it is also possible to fix the fixing device 161 to the body surface 45 without using the adhesive layer.

In other words, the fixing device 161 illustrated in FIG. 12 can also receive the restoring force generated by elasticity of the body wall 41 when inclining the angle of the camera support tube 13 or the cannula 31 at the contact end part between the camera support tube 13 and the cannula 31 in the clamp portion 173, and can use the restoring force as a force (body wall pressing force) which presses the body wall 41 at the contact end part of the body wall 41 in the support table 162.

<Modification Example>

The shape and the material of the dedicated fixing device used in each of the above-described examples, are not particularly limited if fixing to the body surface is possible.

In addition, in each of the above-described examples, a case where each fixing device is fixed to the body surface is described as an example, but the embodiment is not limited thereto.

For example, the camera support tube 13 or the cannula 31 may be fixed by the dedicated fixing device installed on the operating table.

For example, in the fixing device described in each of the above-described examples, a so-called joint arm or an articulated arm which has at least one joint unit, can bend the arm by the joint unit, and can freely change a bending angle, is used, the arm may be fixed to the operating table or to the fixing device installed on the operating table or in the operating room, instead of being fixed to the support table or the body surface 45, and the support table provided with the arm may be fixed to the fixing device installed on the operating table or in the operating room. Accordingly, since it is possible to make the reach from the fixing position of the fixing device to the clamp portion long, effects similar to those in a case where the fixing device is fixed to the body surface 45, which is close to the affected part, can be achieved.

[Embodiment 3]

Still another embodiment of the present invention will be described based on FIG. 14 as follows. In addition, in the embodiment, differences from Embodiments 1 and 2 will be mainly described, configuration elements having the same function as those of the configuration elements used in Embodiment 1 will be given the same reference numerals, and the description thereof will be omitted. In addition, in the embodiment, it is also needless to say that modifications similar to those of Embodiments 1 and 2 are possible.

In Embodiments 1 and 2, a case where the string-like member 38 or the dedicated fixing device (for example, the fixing devices 141, 151, 161, and 171) are used as the fixing tool which fixes the camera support tube 13 inserted into the cannula 31 to the outside of the body, is described as an example, but the fixing tool and the method for fixing the camera support tube 13 are not limited thereto.

In the embodiment, still another example of the fixing tool and the method for fixing the camera support tube 13 will be described.

Figure 14:
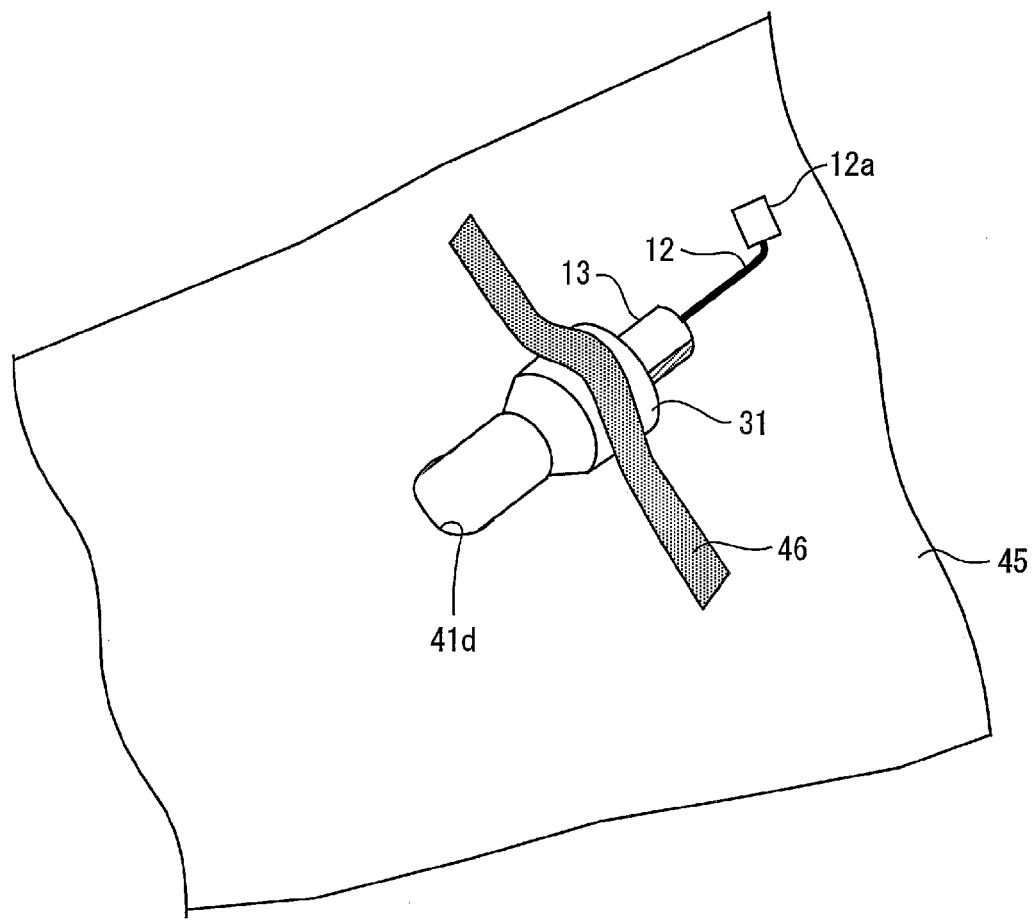
FIG. 14 is a perspective view illustrating an example of a schematic configuration of main parts of a camera system for monitoring the inside of a body according to Embodiment 3.

FIG. 14 is a perspective view illustrating an example of a schematic configuration of main parts of the camera system for monitoring the inside of a body 1 according to the embodiment.

The camera system for monitoring the inside of a body 1 according to the embodiment includes the cannula 31 illustrated in FIGS. 4(a) to 4(c), and an adhesive tape 46 (fixing tool).

In the embodiment, by using the adhesive tape 46 which can be directly fixed to the body surface 45, the camera support tube 13 which is fixed to the cannula 31 is fixed. In addition, in the embodiment, the camera support tube 13 is also indirectly fixed to the body surface 45 via the cannula 31.

As the adhesive tape 46, it is possible to use an adhesive tape which has an adhesive layer in the contact part with the body surface, and is generally used in surgery. The adhesive tape 46 has an adhesive layer, which is not illustrated, on one surface (contact surface with the body surface 45), and can be directly fixed to the body surface 45 due to adhesiveness of the adhesive layer.

In addition, in the embodiment, the practitioner can also operate the camera support tube 13 and can also change the rotational direction or the imaging zoom (distance to the object) of the visual field of the camera unit 11 by easily rotating the camera support tube 13 in the circumferential direction, by pushing the camera support tube 13 to the inside of the body, and by pulling up the camera support tube 13 to the outside of the body.

In the embodiment, by changing the fixing position (that is, a position at which pressure is applied to the cannula 31 by the adhesive tape 46) of the adhesive tape 46 in the cannula 31, it is possible to change the fixing angle (inclination) of the cannula 31 and the camera support tube 13 with respect to the body surface 45. Accordingly, in the embodiment, it is also possible to fix the cannula 31 and the camera support tube 13 at a desirable angle, and to arbitrarily change the direction of the visual field of the camera unit 11.

In addition, for example, below the cannula 31 (that is, between the cannula 31 and the body surface 45), by nipping an object which serves as the fixing height adjustment member which adjusts the fixing height of the cannula 31, and has a desirable thickness similar to the support table 144 illustrated in FIG. 10, the fixing angle (inclination) of the cannula 31 and the camera support tube 13 may be changed. In other words, the camera system for monitoring the inside of a body 1 according to the embodiment may further include a fixing height adjustment member which is not illustrated in addition to the cannula 31 and the adhesive tape 46, as the support tube fixing member.

Accordingly, in the embodiment, it is also possible to fix the camera support tube 13 at a desirable state.

In addition, in the example illustrated in FIG. 14, a case where the cannula 31 is fixed by the adhesive tape 46 by making the adhesive tape 46 adhere to the cannula 31, is illustrated as an example, but in the embodiment, the camera support tube 13 may also be directly fixed by the adhesive tape 46 by making the adhesive tape 46 adhere to the camera support tube 13.

In a case where the camera support tube 13 is directly fixed by the adhesive tape 46, in a case where the position of the camera support tube 13 changes after the practitioner operates the camera support tube 13, adjusts the position of the camera support tube 13, and fixes the camera support tube 13 by the adhesive tape 46, the camera support tube 13 may be fixed by the adhesive tape 46 again after the practitioner peels off the adhesive tape 46, operates the camera support tube 13, and adjusts the position of the camera support tube 13 again.

Accordingly, even in a case where the camera support tube 13 is directly fixed by the adhesive tape 46, it is possible for the camera support tube 13 to be fixed in a desirable state.

In addition, in the embodiment, in a case where the camera support tube 13 is directly fixed by the adhesive tape 46, since the movement of the camera support tube 13 is further restricted by the adhesive tape 46, it is also not necessary that the camera support tube 13 is fixed to the cannula, and a general cannula can be used as the cannula.

[Embodiment 4]

Further still another embodiment of the present invention will be described based on FIGS. 15(a) to 15(c) as follows. In addition, in the embodiment, differences from Embodiments 1 to 3 will be mainly described, configuration elements having the same function as those of the configuration elements used in Embodiment 1 will be given the same reference numerals, and the description thereof will be omitted. In addition, in the embodiment, it is also needless to say that modifications similar to those of Embodiments 1 to 3 are possible.

In Embodiments 1 to 3, a case where the camera support tube 13 or the cannula 31 which is fixed to the camera support tube 13, is fixed to the outside of the body by the fixing tool, is described as an example. In the embodiment, a case where the camera side cable 12 is fixed to the camera support tube 13, and the camera support tube 13 is fixed as the camera side cable 12 is fixed to the outside of the body by the fixing tool, will be described as an example.

FIG. 15(a) is a view in which a sectional view and an upper view of the camera support tube 13 are aligned when the cable fastener 43 is provided at the end part 13b outside the body in the camera support tube 13. FIG. 15(b) is a view in which a sectional view and an upper view of the camera support tube 13 are aligned when the camera side cable 12 passes through the camera support tube 13. FIG. 15(c) is a perspective view illustrating an example of a schematic configuration of main parts of the camera system for monitoring the inside of a body 1 according to the embodiment.

The camera system for monitoring the inside of a body 1 according to the embodiment includes the cannula 31 illustrated in FIGS. 4(a) to 4(c), the cable fastener 43 (cable holder), and the adhesive tape 46 (fixing tool).

As described in Embodiment 1, the camera side cable 12 is connected to the instrument side cable 16 via the camera side cable connector 12a. In the embodiment, in order to lock the camera side cable 12 to the camera support tube 13, as illustrated in FIGS. 15(a) and 15(b), the cable fastener 43 is provided at the end part 13b outside of the body of the camera support tube 13.

<Schematic Configuration of Camera Support Tube 13>

Here, first, a schematic configuration of the camera support tube 13 according to the embodiment will be described.

As illustrated in FIG. 15(a), the camera support tube 13 which is used in the embodiment includes a head portion 113 and a leg portion 114, and has a configuration similar to that of the camera support tube 13 according to Embodiment 1, except that the camera support tube 13 is a funnel-shaped tube in which the inner diameter of the head portion 113 is greater than the inner diameter of the leg portion 114.

The end part 13a on the leg portion 114 side of the camera support tube 13 according to the embodiment is inserted into the body through the body wall 41, such as an abdominal wall.

Therefore, as the camera support tube 13, in a state where the camera support tube 13 is inserted into the cannula 31, the camera support tube 13 including the leg portion 114 of which the length in the axial direction is longer than that of the leg portion 132 of the cannula 31 is used so that the end part 13a on the leg portion 114 side which is an end part on a side inserted into the body, and the end part 13b on the head portion 113 side which is an end part outside the body, are exposed from the cannula 31. In addition, the camera support tube 13 which has the size (thickness) to have a void between the outer wall of the camera support tube 13 and the inner wall of the cannula 31 in a state where the camera support tube 13 is inserted into the cannula 31 so that the camera support tube 13 can be rotated inside the cannula 31.

In addition, in the embodiment, the leg portion 114 of the camera support tube 13 also has a cylindrical shape. Therefore, in the embodiment, as the cannula 31, the cannula 31 illustrated in FIGS. 4(a) to 4(c) is used, but it is easy to combine the leg portion 114 with a general cannula which is a cylindrical tube.

<Schematic Configuration of Cable Fastener 43>

As described above, the camera support tube 13 which is used in the embodiment has a shape in which the end part 31b (outside the body) on the head portion 113 side is thicker than the end part 31a on the leg portion 114 side (inside the body) inserted in the body.

The cable fastener 43 is provided at the end part 31b on the head portion 113 side in the camera support tube 13.

As illustrated in FIGS. 15(a) and 15(b), the cable fastener 43 has a longitudinal groove 43a which extends in the axial direction of the camera support tube 13, and of which the width narrows (a lateral section is tapered in the outward orientation) to the outside (a direction of a side surface) from the center of the camera support tube 13. In addition, as the longitudinal groove 43a, instead of providing the tapered longitudinal groove in the cable fastener 43, the cable fastener 43 is configured of the elastic member, and by providing a cut-out as the longitudinal groove 43a in the cable fastener 43, the camera side cable 12 may also be held using the biasing force by the elastic material.

According to the embodiment, in this manner, by fixing the camera side cable 12 to a bottom unit (a part of which the width decreases) of the longitudinal groove 43a of the cable fastener 43, it is possible to fix the camera side cable 12 to the camera support tube 13.

Therefore, according to the embodiment, after the camera side cable 12 and the camera support tube 13 are fixed by the cable fastener 43 as illustrated in FIG. 15(b), by fixing the camera side cable 12 by the adhesive tape 46 or the like as illustrated in FIG. 15(c), it is possible to fix the position of the camera support tube 13.

In addition, the cable fastener 43 may be integrally formed with the camera support tube 13, and may be separately formed. In other words, the camera side cable 12 may be fixed by inserting the cable fastener 43 into the camera support tube 13 as a separated component after the camera side cable 12 passes through the camera support tube 13.

<Result>

In the embodiment, after the practitioner operates the camera support tube 13, adjusts the position of the camera support tube 13, and fixes the camera side cable 12 by the adhesive tape 46, in a case where the position of the camera support tube 13 is changed, the camera side cable 12 may also be fixed by the adhesive tape 46 again after the practitioner peels off the adhesive tape 46, operates the camera support tube 13, and adjusts the position of the camera support tube 13 again.

In addition, for example, below the camera side cable 12 (that is, between the camera side cable 12 and the body surface 45), or below the cannula 31 or the camera support tube 13 according to the situation, as the fixing height adjustment member, by nipping the object having a desirable thickness similar to the support table 144 illustrated in FIG. 10, the fixing angle (inclination) of the cannula 31 connected to the camera side cable 12 and the camera support tube 13 may be changed. In other words, in the embodiment, the support tube fixing member may also be additionally provided with the fixing height adjustment member which is not illustrated.

Accordingly, even in a case where the camera side cable 12 is directly fixed by the adhesive tape 46, it is possible for the camera support tube 13 to be fixed in a desirable state.

In addition, according to the embodiment, by fixing the camera side cable 12 to the camera support tube 13 using the cable fastener 43, it is possible to temporarily stop the camera side cable 12 in the middle of the installation work of the camera unit 11, and there is an advantage that workability is improved. In addition, even when the camera side cable 12 is pulled to the outside of the body after the installation, the load is not applied to the connection part of the camera unit and the camera side cable 12, and there is also an advantage that it is possible to prevent the camera side cable from being broken.

<Modification Example>

In the embodiment, as described above, a case where the cannula 31 illustrated in FIGS. 4(a) to 4(c) is used as the cannula 31, is also described as an example. However, it is not necessary for the camera support tube 13 according to the embodiment to be fixed to the cannula, and a general cannula can be used as the cannula.

In other words, in the embodiment, by fixing the camera side cable 12 to the camera support tube 13, and fixing the camera side cable 12 to the outside of the body, it is possible to fix the camera support tube 13 by the camera side cable 12. In other words, by fixing the camera side cable 12 by the adhesive tape 46, the position and the orientation of the camera support tube 13 connected to the camera side cable 12 are fixed. Therefore, similar to a case where the camera support tube 13 is fixed to the outside of the body directly by the fixing tool, the camera support tube 13 may not be fixed to the cannula.

In addition, in the embodiment, as described above, a case where the camera support tube 13 is fixed by fixing the camera side cable 12 to the camera support tube 13 by using the cable fastener 43, and by fixing the camera side cable 12 to the outside of the body by the adhesive tape 46, will be described as an example. However, the embodiment is not limited thereto, and after fixing the camera side cable 12 to the camera support tube 13 by using the cable fastener 43 as described above, the camera support tube 13 or the cannula 31 may be fixed to the outside of the body by fixing the camera side cable 12 thereto by the fixing tool, such as the adhesive tape. It is needless to say that two or more among the camera side cable 12, the camera support tube 13, and the cannula 31 may be fixed. In any case, by fixing the camera side cable 12 to the camera support tube 13 using the cable fastener 43, an effect that it is possible to improve workability as described above, and to prevent the camera side cable from being broken, can be achieved.

In addition, in the embodiment, a case where the adhesive tape 46 is used in fixing the camera side cable 12, or the camera support tube 13 or the cannula 31, will be described.

However, the fixing tool is not limited thereto, and it is needless to say that a fixing tool similar to the fixing tool used in fixing the camera support tube 13 or the cannula 31 in Embodiments 1 to 3 can be used.

[Embodiment 5]

Further still, another embodiment of the present invention will be described based on FIGS. 16(*a*) to 16(*d*), and FIGS. 17(*a*) to 17(*h*) as follows. In addition, in the embodiment, differences from Embodiments 1 to 4 will be mainly described, configuration elements having the same function as those of the configuration elements used in Embodiment 1 will be given the same reference numerals, and the description thereof will be omitted. In addition, in the embodiment, it is also needless to say that modifications similar to those of Embodiments 1 to 4 are possible.

In Embodiments 1 to 4, a case where the camera support tube 13 and the cannula 31 are separated from each other, is described as an example. In the embodiment, a case where the camera support tube 13 is directly fixed to the body surface without using the cannula 31 by giving a function of the cannula to the camera support tube 13, will be described as an example.

<Schematic Configuration of Camera Support Tube 13>

Figure 16:
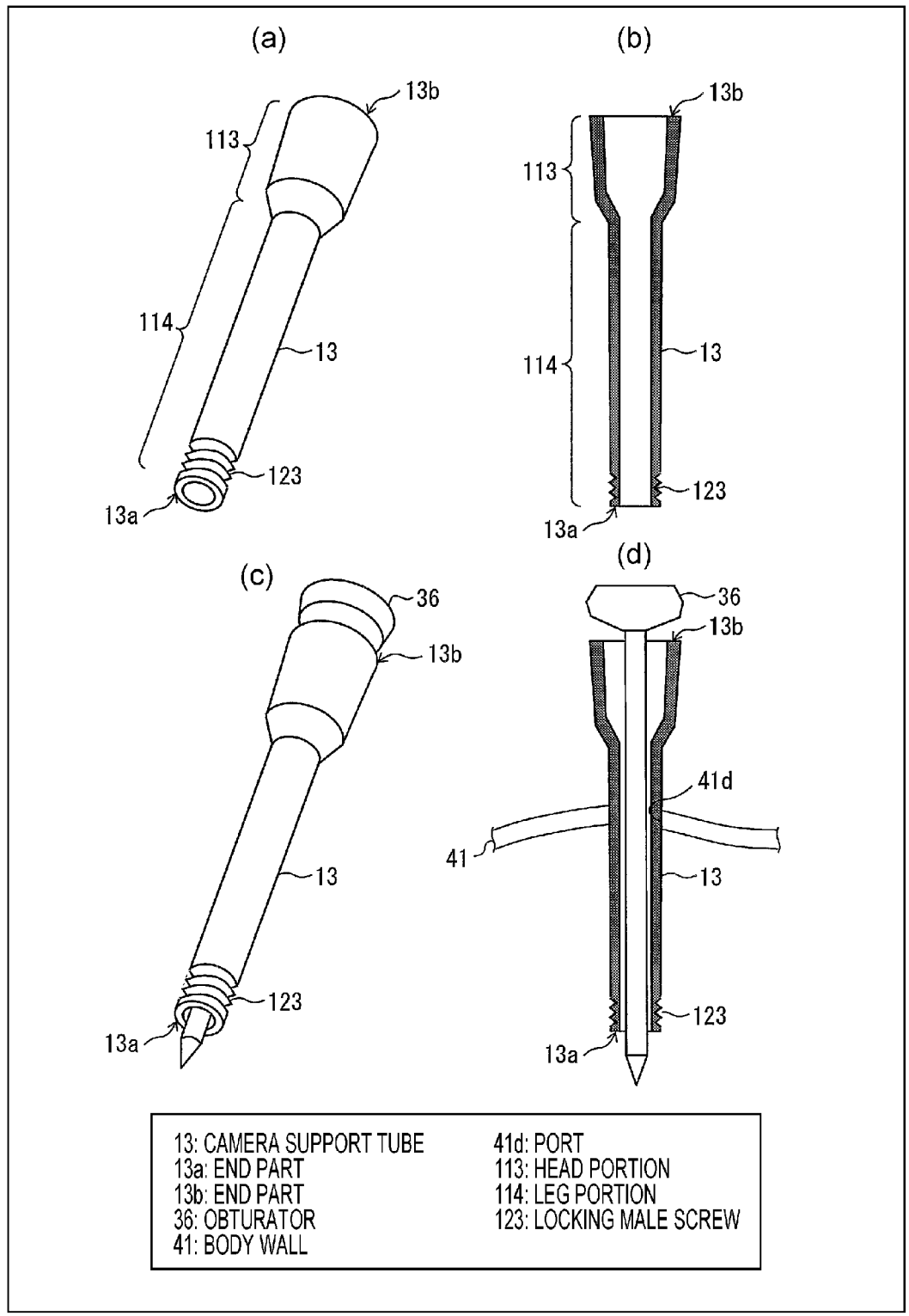
FIG. 16(a) is a perspective view of a camera support tube according to Embodiment 5.
FIG. 16(b) is a sectional view of the camera support tube illustrated in FIG. 16(a).
FIG. 16(c) is a perspective view of a case where the camera support tube according to Embodiment 5 is combined with an obturator.
FIG. 16(d) is a sectional view illustrating a state where the camera support tube according to Embodiment 5 is punctured through a body wall.

FIG. 16(*a*) is a perspective view of the camera support tube 13 according to Embodiment 5. FIG. 16(*b*) is a sectional view of the camera support tube 13 illustrated in FIG. 16(*a*). FIG. 16(*c*) is a perspective view of a case where the camera support tube 13 according to embodiment is combined with an obturator. FIG. 16(*d*) is a sectional view illustrating a state where the camera support tube 13 according to embodiment is punctured through the body wall 41.

<Schematic Configuration of Camera Support Tube 13>

Here, first, a schematic configuration of the camera support tube 13 according to the embodiment will be described.

Figure 15:
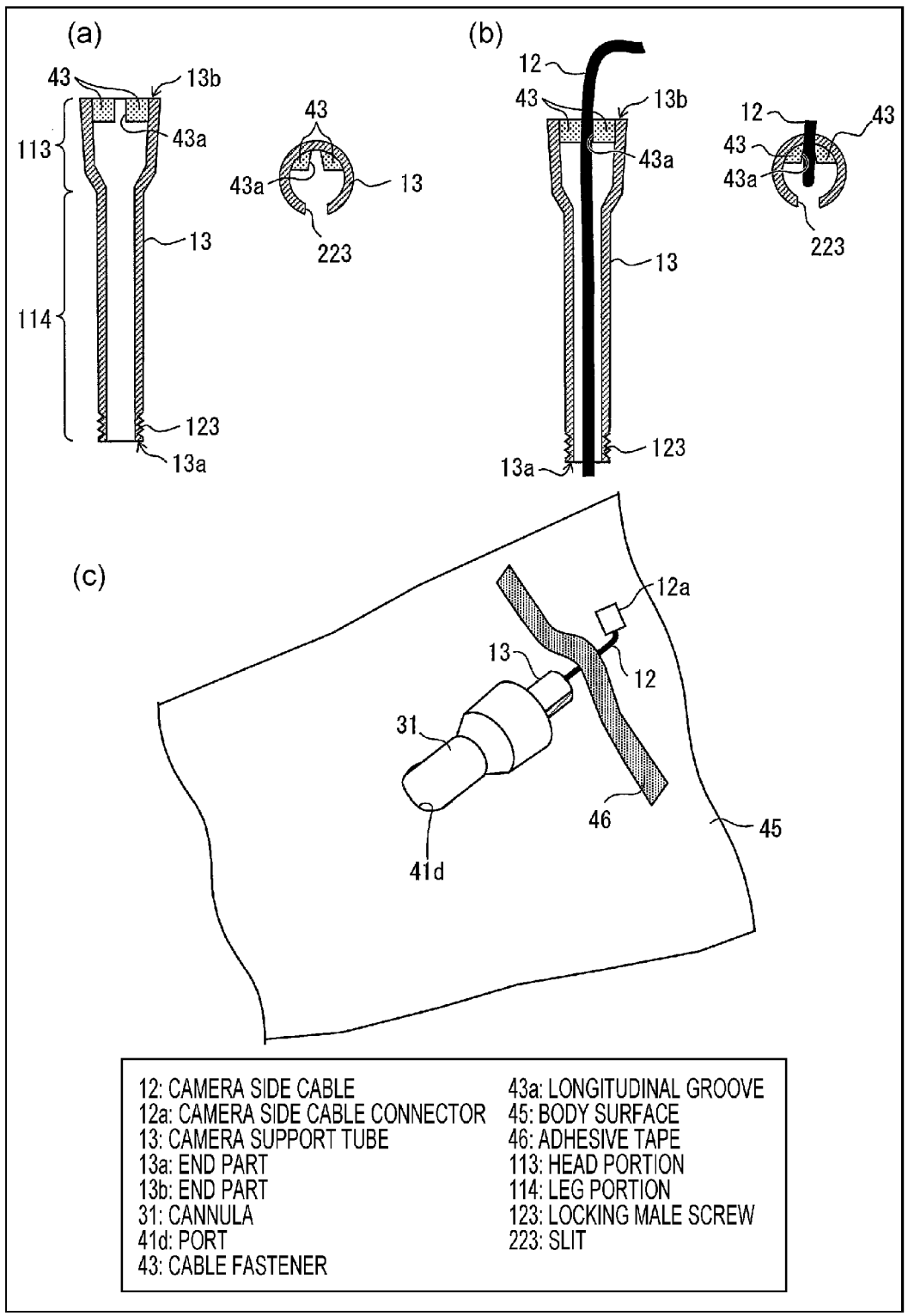
FIG. 15(a) is a view in which a sectional view and an upper view of a camera support tube are aligned when a cable fastener is provided at an end part outside the body in a camera support tube according to Embodiment 4.
FIG. 15(b) is a view in which a sectional view and an upper view of the camera support tube are aligned when a camera side cable passes through the camera support tube.
FIG. 15(c) is a perspective view illustrating an example of a schematic configuration of main parts of the camera system for monitoring the inside of a body according to Embodiment 4.

As illustrated in FIG. 15(*a*), the camera support tube 13 which is used in the embodiment is a funnel-shaped tube which includes the head portion 113 and the leg portion 114, and in which the inner diameter of the head portion 113 is greater than the inner diameter of the leg portion 114, and has a configuration similar to that of the camera support tube 13 according to Embodiment 1, except that the slit 223 is not provided.

The end part 13*a* on the leg portion 114 side of the camera support tube 13 according to the embodiment is directly inserted into the body through the body wall 41, such as an abdominal wall.

In the embodiment, the camera support tube 13 in which the length of the leg portion 114 in the axial direction is longer than the thickness of the body wall 41, and the length that can freely move the leg portion 114 in the axial direction inside the body, is also used as the camera support tube 13 so that the practitioner can change the imaging zoom (distance to the object) by operating the camera support tube 13 exposed to the outside of the body, by pressing the camera support tube 13 to the inside of the body, and by pulling up the camera support tube 13 to the outside of the body.

In addition, it is desirable that the camera support tube 13 in which the leg portion 114 is a cylindrical tube is used as the camera support tube 13 so that it is possible to freely rotate the camera support tube 13 at a desirable height.

However, the embodiment is not limited thereto, and the camera support tube 13 may be provided to be movable and rotatable in the axial direction inside the body.

In addition, from the viewpoint of low invasiveness, it is preferable that the diameter of the camera support tube 13 is as small as possible.

According to the embodiment, as illustrated in FIGS. 16(*c*) and 16(*d*), in a case where the camera support tube 13 is inserted into the body, an obturator 36 (sharpened rod) is inserted into the camera support tube 13, and a tip end (sharp part) of the obturator 36 exposed from the end part 13*a* inside the body of the camera support tube 13 is punctured through the port 41*d* opened on the body wall 41. Accordingly, the camera support tube 13 is inserted into the port 41*d*, and the camera support tube 13 is contact-fixed by the body wall 41. In addition, since the end part 13*b* on the head portion 113 side of the camera support tube 13 protrudes to the outside of the body, as the head portion 113 functions as a stopper, the camera support tube 13 does not fall out of the body.

<Method for Installing Camera System for Monitoring inside of Body 1>

Next, both the method for installing the imaging apparatus 2 in the camera system for monitoring the inside of a body 1 according to the embodiment, and the method of use, will be described.

Figure 17:
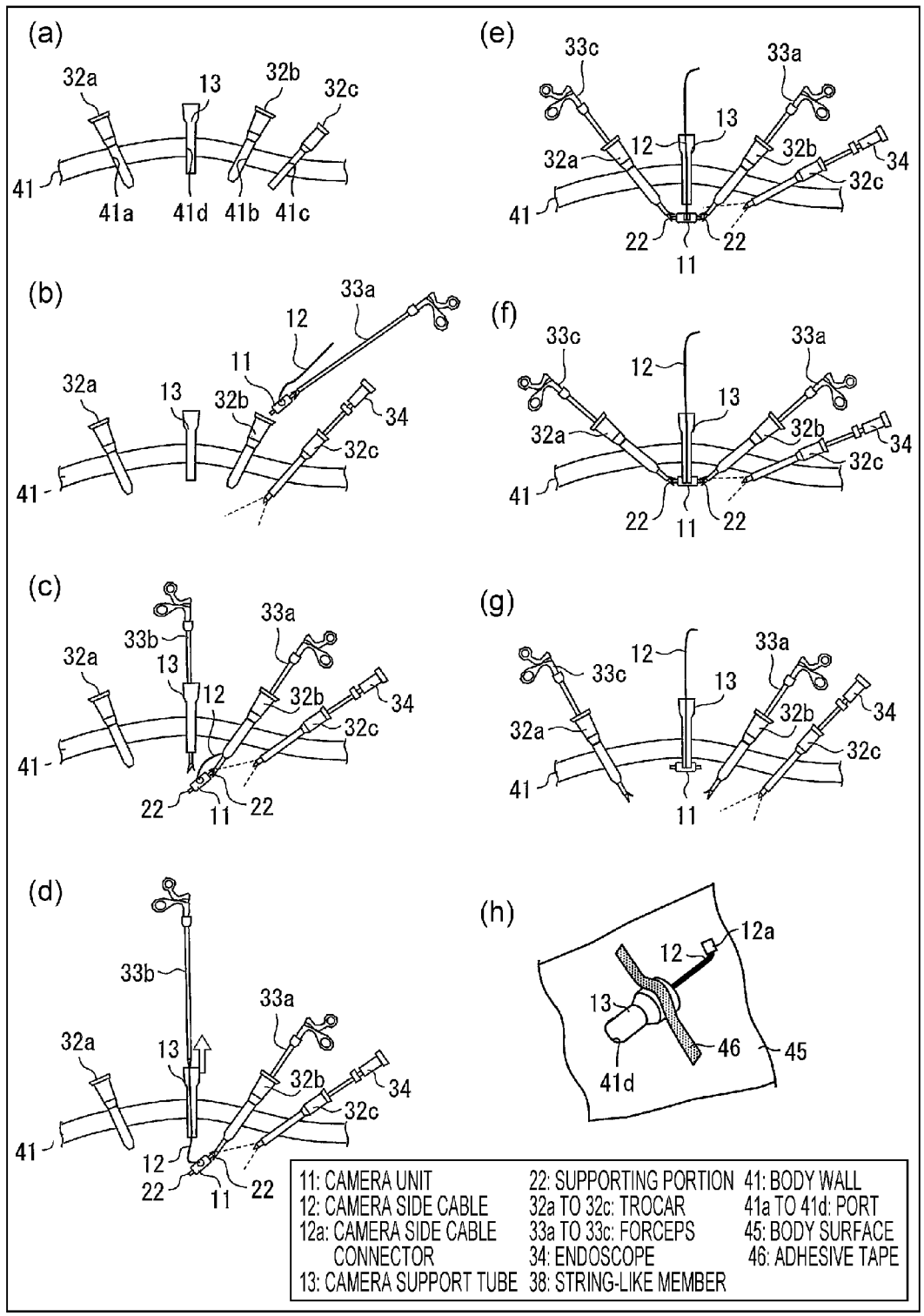
FIGS. 17(a) to 17(h) are schematic views illustrating a method for installing an imaging apparatus in the camera system for monitoring the inside of a body according to Embodiment 5.

FIGS. 17(*a*) to 17(*h*) are schematic views illustrating the method for installing the imaging apparatus 2 in the camera system for monitoring the inside of a body 1 according to the embodiment.

Figure 5:
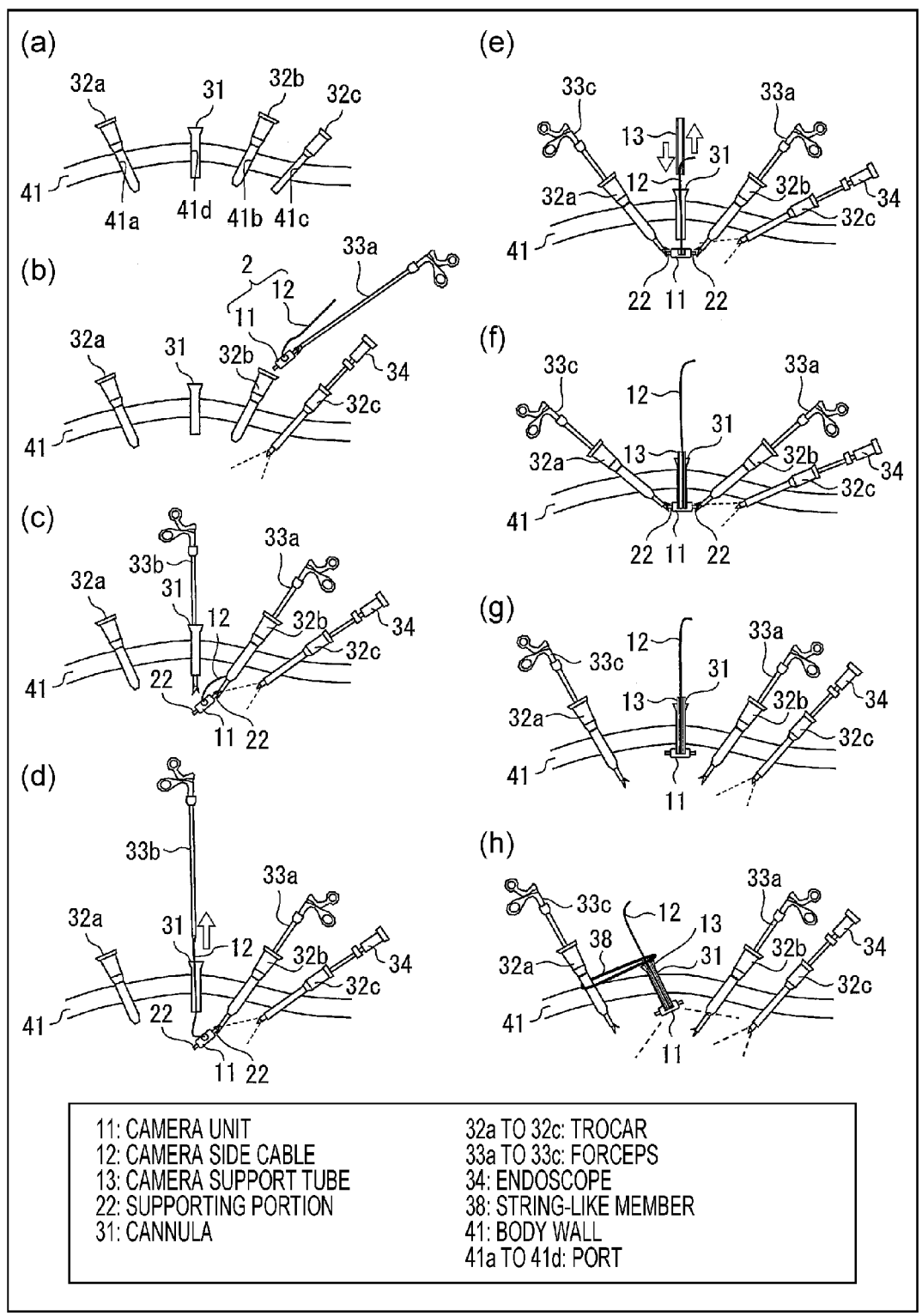
FIGS. 5(a) to 5(h) are schematic views illustrating a method for installing the imaging apparatus in the camera system for monitoring the inside of a body according to Embodiment 1 in order of process.
Figure 6:
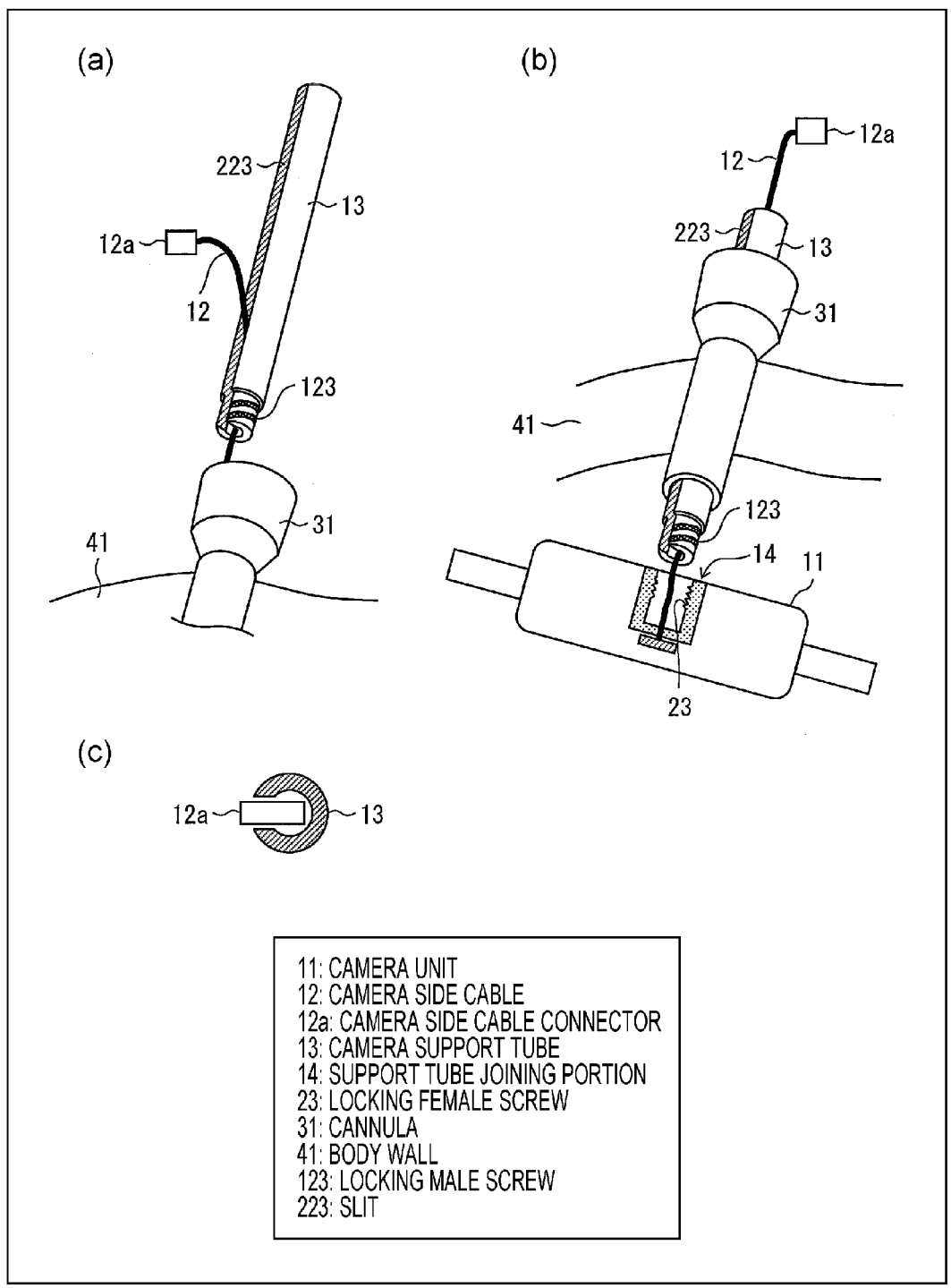
FIGS. 6(a) and 6(b) are perspective views illustrating the process illustrated in FIG. 5(e) in detail.
FIG. 6(c) is a plan view illustrating a relationship between the size of a cable connector and the size of the camera support tube in the camera system for monitoring the inside of a body according to the embodiment.

First, as illustrated in FIG. 17(*a*), similar to FIG. 5(*a*), the practitioner opens the ports 41*a* to 41*c* (holes) on the body wall 41 for inserting the forceps or the endoscope into the body cavity, and inserts each of the plurality of trocars 32 (hereinafter, referred to as the trocars 32*a* to 32*c*) into the ports 41*a* to 41*c*.

Furthermore, in order to install the camera unit 11 in the body cavity, on the body wall 41, the port 41*d* is opened at a position where the entire organ including the affected part can be seen, and instead of the cannula 31, the camera support tube 13 is inserted into the port 41*d* as illustrated in FIGS. 15(*a*) to 15(*d*). Specifically, as illustrated in FIGS. 15(*c*) and 15(*d*), in a state where the needle-like obturator 36 passes through the inside of the camera support tube 13, the obturator 36 is punctured through the port 41*d*. Accordingly, as illustrated in FIG. 15(*d*), the camera support tube 13 is inserted into the body wall 41, and is contact-fixed by the body wall 41. After this, the obturator 36 is extracted from the camera support tube 13.

After at least one of the trocars 32*a* to 32*c* is inserted, the practitioner sends gas into the body through the trocar, expands the inside of the body cavity in advance, and ensures the space into which the device is inserted.

Next, as illustrated in FIG. 17(*b*), the practitioner inserts the endoscope 34 into the body cavity through the trocar 32*c*, grips the supporting portion 22 by the forceps 33*a* while observing the inside of the body using the endoscope 34, and inserts the imaging apparatus 2 into the body cavity through the trocar 32*b*.

Next, as illustrated in FIG. 17(*c*), the practitioner operates the forceps 33*a*, moves the imaging apparatus 2 to be close to the camera support tube 13, and inserts the forceps 33*b* into the body cavity through the camera support tube 13.

Next, as illustrated in FIG. 17(*d*), the practitioner leads the camera side cable 12 to the outside of the body by pulling out the forceps 33*b* from the camera support tube 13 in a state where the camera side cable 12 is nipped by the forceps 33*b*. At this time, the supporting portion 22 in the camera unit 11 is gripped by the forceps 33*a*.

Next, as illustrated in FIG. 17(*e*), the practitioner inserts the forceps 33*c* into the body cavity through the trocar 32*a*, and grips the supporting portions 22 on both side surfaces of the camera unit 11 by two forceps 33*a* and 33*c* so that the support tube joining portion 14 of the camera unit 11 and the opening of the camera support tube 13 becomes parallel and close to each other.

Next, as illustrated in FIG. 17(f), the practitioner inserts the end part 13a inside the body of the camera support tube 13 into the support tube joining portion 14 of the camera unit 11, and screws the end part 13a. Accordingly, in a state where the camera side cable 12 passes through the inside of the camera support tube 13, the camera support tube 13 and the camera unit 11 join with each other at the support tube joining portion 14, inside the body.

Next, as illustrated in FIG. 17(g), the practitioner pulls up the camera support tube 13 so that the widest area possible inside of the body cavity can be imaged.

Next, the height, the orientation, and the angle in the body cavity of the camera unit 11 is determined by operating the camera support tube 13, and as illustrated in FIG. 17(h), the camera support tube 13 is fixed by the fixing tool, such as the adhesive tape 46. Accordingly, even when the practitioner does not support the camera support tube 13, it is possible to maintain the state of the camera support tube 13.

After installing the camera unit 11 in the body, similar to Embodiment 1, the camera side cable 12 and the instrument side cable 16 are joined to each other by using the camera side cable connector 12a.

<Effect>

As described above, in the embodiment, similar to Embodiments 1 to 4, the camera unit 11 and the camera support tube 13 also join with each other with high mechanical strength, and a supporting force of the camera unit 11 is higher than that in the related art. In addition, since the camera side cable 12 is guided toward the outside of the body through the inside of the camera support tube 13, after the camera unit 11 and the camera support tube 13 join with each other, the load is not applied to the camera side cable 12, the camera side cable 12 is not exposed to the inside of the body, and the camera side cable 12 does not come into contact with the body wall 41. Accordingly, certainty (waterproof and stainproof properties of the connected part) of the electric connection of the camera side cable 12 and the circuit board 19 is increased. Therefore, it is possible to realize the camera system for monitoring the inside of a body 1 having high reliability.

In the embodiment, similar to Embodiments 1 to 4, the practitioner can also operate the camera support tube 13, arbitrarily set the direction of the visual field, the rotational direction of the visual field, and the imaging zoom (distance to the object) of the camera unit 11, and fix the camera unit 11 at a desirable position. Therefore, it is possible to realize a camera system for monitoring the inside of a body having high usability.

Additionally, according to the embodiment, it is not necessary to pass through the camera support tube 13 inside similar to the cannula 31 of Embodiments 1 to 4, the camera support tube 13 is directly inserted into the body wall 41, and the camera support tube 13 can be directly fixed to the body surface. Therefore, it is possible to reduce the diameter of the port 41d. Due to this, the embodiment is excellent from the viewpoint of low invasiveness. In addition, according to the embodiment, since the process in which the camera support tube 13 passes through the cannula 31 in a state where the camera side cable 12 passes through the camera support tube 13 as described in Embodiment 1, is not necessary, the work efficiency of the practitioner can be improved.

<Modification Example>

In addition, in FIG. 17(h), a case where the adhesive tape 46 is used as the fixing tool, is illustrated as an example, but the fixing tool is not limited thereto, and it is needless to say that the dedicated fixing device described in Embodiments 2 and 3 may be used as the fixing tool.

In Embodiment 4, a case where the camera support tube 13 is fixed to the body surface in a state where the camera support tube 13 is inserted into the cannula 31, will be described. However, as illustrated in the embodiment, after the camera support tube 13 is punctured through the body wall 41 using the obturator, and the camera side cable 12 passes through the camera support tube 13, the cable fastener 43 may be inserted into the camera support tube 13 as a separate component. Accordingly, even in a case where the camera support tube 13 is fixed using the camera side cable 12 as illustrated in Embodiment 4, it is possible to directly fix the camera support tube 13 to the body surface without using the cannula 31.

In addition, even in a case where the string-like member is used as the fixing tool, by using the plurality of string-like members or the string-like member having branch portions, it is possible to directly fix the camera support tube 13 to the body surface without using the cannula 31.

In this case, for example, as illustrated in FIGS. 16(a) to 16(d), the camera support tube 13 including the head portion 113 which functions as a stopper that prevents the camera support tube 13 from falling out of the body is used as the camera support tube 13, the camera support tube 13 is hung by using the string-like member, and locked to the trocar or the like as described in Embodiment 1, and accordingly, it is possible to directly fix the camera support tube 13 to the body surface in a state where the length, the rotational direction, and the inclination with respect to the body surface of the camera support tube 13 inside the body are held.

In addition, instead of using the camera support tube 13 illustrated in FIGS. 16(a) to 16(d), as the camera support tube 13, even when a string-like member fixing unit (for example, a fixing unit which can fix the string-like member by making the string-like member pass or by binding the string-like member) which prevents the movement of the string-like member of the camera support tube 13 in the axial direction is provided in the camera support tube 13, similar effects can be obtained.

[Embodiment 6]

Further still, another embodiment of the present invention will be described based on FIGS. 18 to 23 as follows. In addition, in the embodiment, differences from Embodiments 1 to 4 will be mainly described, configuration elements having the same function as those of the configuration elements used in Embodiment 1 will be given the same reference numerals, and the description thereof will be omitted. In addition, in the embodiment, it is also needless to say that modifications similar to those of Embodiments 1 to 4 are possible.

In Embodiments 1 to 4, a case where the camera support tube 13 and the cannula 31 to which the camera support tube 13 is fixed are fixed to the outside of the body by the fixing tool, or a case where the camera side cable 12 is fixed to the camera support tube 13 and the camera support tube 13 is fixed by fixing the camera side cable 12 to the outside of the body by using the fixing tool, are described as an example. In the embodiment, in the cases, an example in which an air plug (accessory for a support tube) which has a function of fully filling the space between the camera support tube 13 and the cannula 31, that is, a function of blocking at least a part of the void between the camera support tube 13 and the cannula 31, is used, will be described.

<Air Plug>

Figure 18:
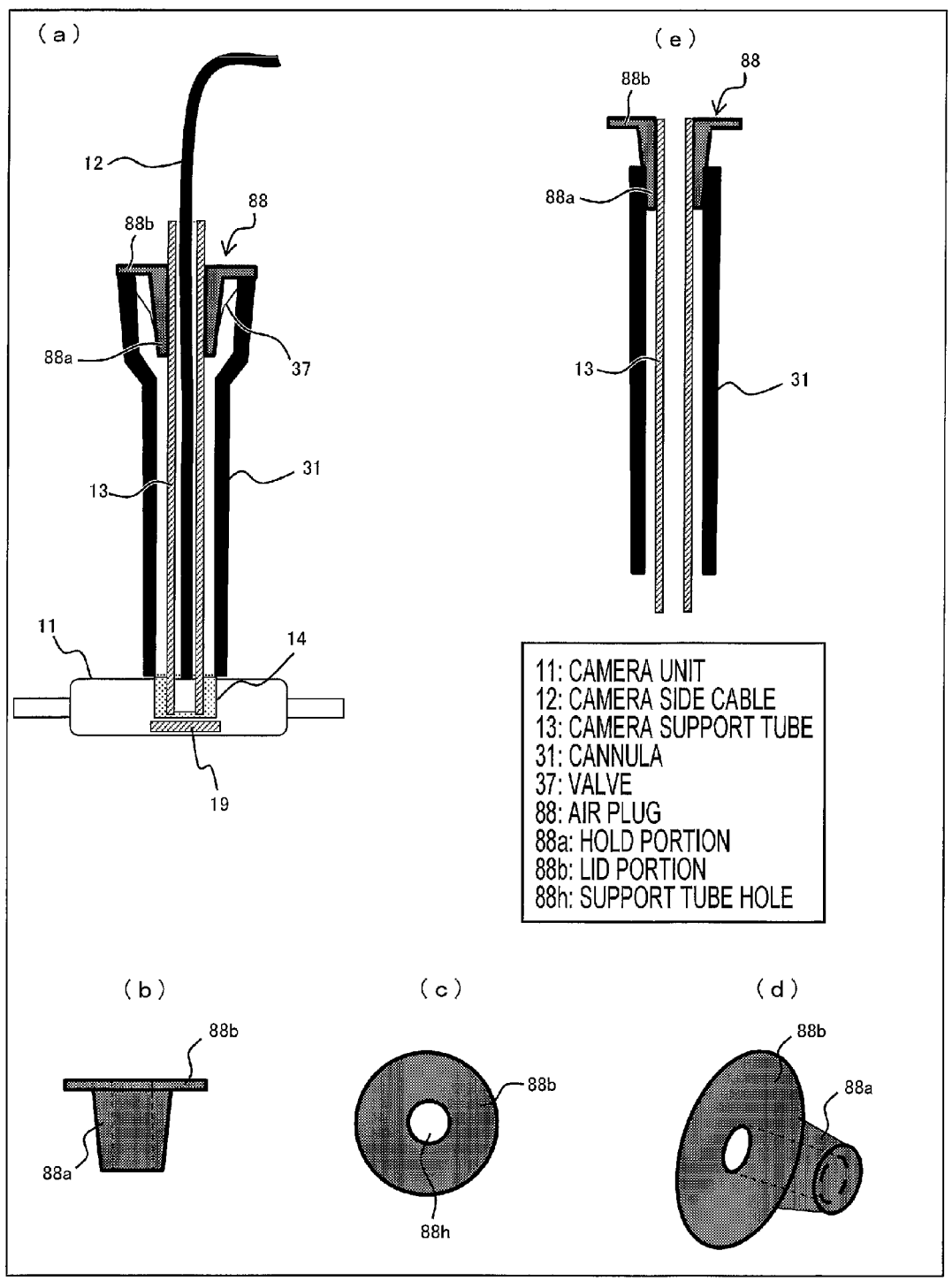
FIGS. 18(a) to 18(e) are schematic views illustrating a structure of an air plug according to Embodiment 6.

FIG. 18(*a*) is a sectional view illustrating a state where an air plug 88 is provided between the end part outside the body in the camera support tube 13 and the end part outside the body in the cannula 31, in a sectional view illustrating a joined state of the camera support tube 13 inserted into the cannula 31 and the camera unit 11. FIG. 18(*b*) is a side view of the air plug 88. FIG. 18(*c*) is an upper view of the air plug 88. FIG. 18(*d*) is a perspective view of the air plug 88. FIG. 18(*e*) is a sectional view in a case where the size of the end part outside the body in the cannula 31 is small.

The tube-like member, such as the cannula or the trocar which installs the camera support tube 13, has various types of sizes of the inner diameter, and inner structures, such as the valve. Therefore, when installing the camera support tube 13 in the tube-like member, according to the type of the tube-like member, there is a case where gas which inflates the abdominal wall leaks from the void between the camera support tube 13 and the tube-like member 31, and a defect is generated. Therefore, as illustrated in FIG. 18(*a*), it is effective to provide the air plug 88 (accessory for the support tube) which reduces the leakage between the tube-like member 31 and the camera support tube 13.

The air plug 88 of FIGS. 18(*a*) to 18(*d*) includes a hold portion 88*a* and a flange-like lid portion 88*b*, and the hold portion 88*a* has a shape of a tapered (becomes narrow when approaching the body surface side) truncated cone, and is provided with a support tube hole 88*h* which passes through the hold portion 88*a*. The air plug 88 configured of an elastic material, such as rubber, is disposed to be fitted into the upper end part of the cannula 31 (tube-like member) so that the hold portion 88*a* pressingly expands a valve 37, and to cover the upper surface of the cannula 31 with the lid portion 88*b*, in a state where the camera support tube 13 is held in the support tube hole 88*h*. As described above, the air plug 88 substantially blocks the void between the cannula 31 and the camera support tube 13.

In addition, since the void (void which is greater than that in a case where the small number, such as one or two, of valves 37, or in a case where the inner diameter of the cannula 31 is large) which is generally large between the valve 37 of the cannula 31 and the camera support tube 13 is generated, the air plug 88 is necessary in reducing the leakage of the air. This is also employed in the following modification example of the air plug.

FIG. 18(*a*) illustrates an example in which the valve 37 comes into contact with the air plug 88 at the upper part of the cannula 31, but this is merely an example. It is needless to say that the air plug 88 also achieves an effect of reducing the air leakage in a case where the valve 37 and the air plug 88 does not come into contact with each other, such as a case where the valve 37 is not at the upper part of the cannula 31. This is also employed in the following modification example of the air plug.

In FIG. 18(*a*), an example in which the upper part of the cannula 31 is installed at a relatively large part, is illustrated. As the lower part of the hold portion 88*a* gradually becomes narrow as illustrated in FIG. 18(*b*), even in a case where the upper part of the cannula 31 is narrower than this (illustrated in FIG. 18(*e*)), it is possible to perform the insertion so that the outer side surface of the lower part of the hold portion 88*a* comes into contact with the inner side surface of the upper end part of the cannula 31, and to employ this as the air plug with respect to various types of the cannula (tube-like member).

In addition, it is not necessary to completely seal (completely block the void between the camera support tube 13 and the cannula 31) in the cannula 31 by the air plug 88, and it is sufficient if it is possible to prevent large leakage which deflates the inflated body cavity. It is desirable that the void somewhat remains and gas appropriately leaks since there is an effect of reducing the temperature inside the body. In addition, since this causes cooling of the camera support tube 13, it is possible to improve the effect of releasing the heat of the camera unit 11 to the air via the camera support tube 13.

<Air Plug-cum-Support Tube Holder>

The air plug can also function as a support tube holder which holds and fixes the support tube to the cannula.

Figure 19:
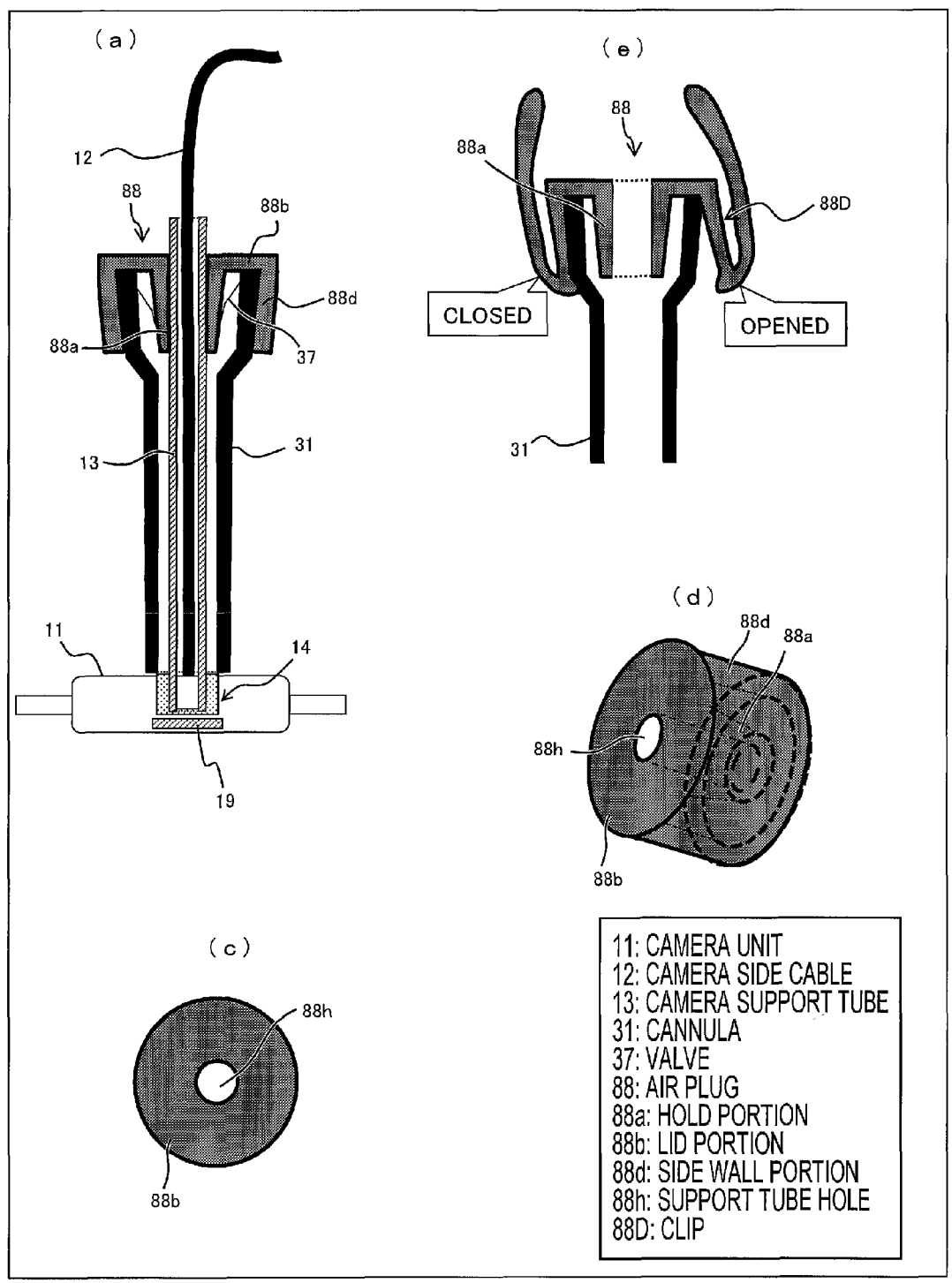
FIGS. 19(a) to 19(e) are schematic views illustrating a structure of the air plug (having a function of a support tube holder) according to Embodiment 6.

FIG. 19(*a*) is a sectional view illustrating a state where the air plug having a function of holding the support tube is provided between the end part outside the body in the camera support tube 13 and the end part outside the body in the cannula 31, in a sectional view illustrating the joined state of the camera support tube 13 inserted into the cannula 31 and the camera unit 11. FIG. 19(*c*) is an upper view of the air plug. FIG. 19(*d*) is a perspective view of the air plug. FIG. 19(*e*) is another example in which a plate spring-like clip for fixing the support tube is attached to the side surface of the air plug. As illustrated in FIGS. 19(*a*), 19(*c*) and 19(*d*), the air plug 88 (accessory for the support tube, support tube holder) includes the hold portion 88*a*, the flange-like lid portion 88*b*, and a side wall portion 88*d* which extends to the body surface side from a circumferential edge of the lid portion 88*b*, and the hold portion 88*a* has a shape of a tapered (becomes narrow when approaching the body surface side) truncated cone, and is provided with the support tube hole 88*h* which passes through the hold portion 88*a*. The air plug 88 configured of an elastic member, such as one made of rubber, is disposed to be fitted into the upper end part of the cannula 31 so that the hold portion 88*a* pressingly expands the valve 37, to cover the upper surface of the upper end part of the cannula 31 with the lid portion 88*b*, and to cover the outer side surface of the upper end part of the cannula 31 with the side wall portion 88*d*, in a state where the camera support tube 13 is held in the support tube hole 88*h*. As described above, the air plug 88 substantially blocks the void between the cannula 31 and the camera support tube 13, and fixes the camera support tube 13 and the cannula 31.

As described in FIG. 19(*e*), a structure in which the cannula 31 is nipped by opening and closing the clip using a clip 88D, such as a plate spring, instead of the side wall portion 88*d*, can be employed. According to such a clip structure, it is possible to employ various types of cannulas (tube-like members) having different sizes from each other, and versatility is improved.

<Air Plug-cum-Cable Holder>

The air plug can also function as a cable holder which holds and fixes the camera side cable to the support tube.

Figure 20:
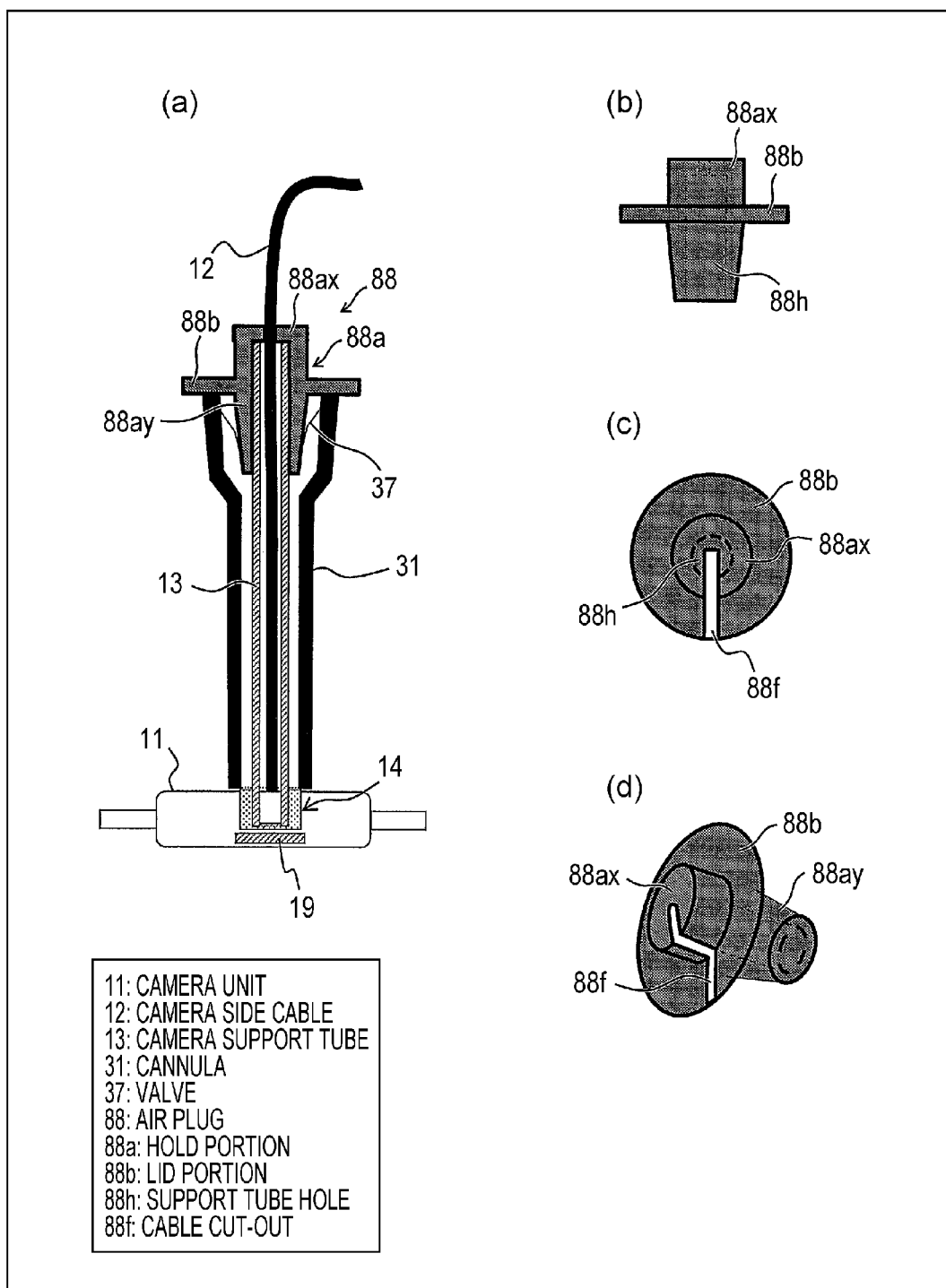
FIGS. 20(a) to 20(d) are schematic views illustrating a structure of the air plug (having a function of a cable holder) according to Embodiment 6.

FIG. 20(*a*) is a sectional view illustrating a state where the air plug having a function of a cable holder is provided between the end part outside the body in the camera support tube 13 and the end part outside the body in the cannula 31, in a sectional view illustrating the joined state of the camera support tube 13 inserted into the cannula 31 and the camera unit 11. FIG. 20(*b*) is a side view of the air plug. FIG. 20(*c*) is an upper view of the air plug. FIG. 20(*d*) is a perspective view of the air plug.

As illustrated in FIGS. 20(*a*) to 20(*d*), the air plug 88 (accessory for the support tube, cable holder) includes the hold portion 88*a* and the flange-like lid portion 88*b*, the hold portion 88*a* includes an upper part 88*ax* positioned above the lid portion 88b in a columnar shape and a lower part 88ay positioned below the lid portion 88b (body surface side) in a shape of a tapered (becomes narrow when approaching the body surface side) truncated cone, the support tube hole 88h is provided in the hold portion 88a, and a cable cut-out 88f which reaches the circumferential edge of the lid portion 88b from the center part of the upper part 88ax is provided. The air plug 88 configured of an elastic member, such as one made of rubber, is disposed to be fitted into the upper end part of the cannula 31 (tube-like member) so that the lower part 88ay pressingly expands the valve 37, and to cover the upper surface of the upper end part of the cannula 31 with the lid portion 88b, in a state where the camera side cable 12 which passes through the cable cut-out 88f is held at the center of the upper part 88ax, and the camera support tube 13 is held in the support tube hole 88h. As described above, the air plug 88 substantially blocks the void between the cannula 31 and the camera support tube 13, and fixes the camera support tube 13 and the camera side cable 12.

Figure 21:
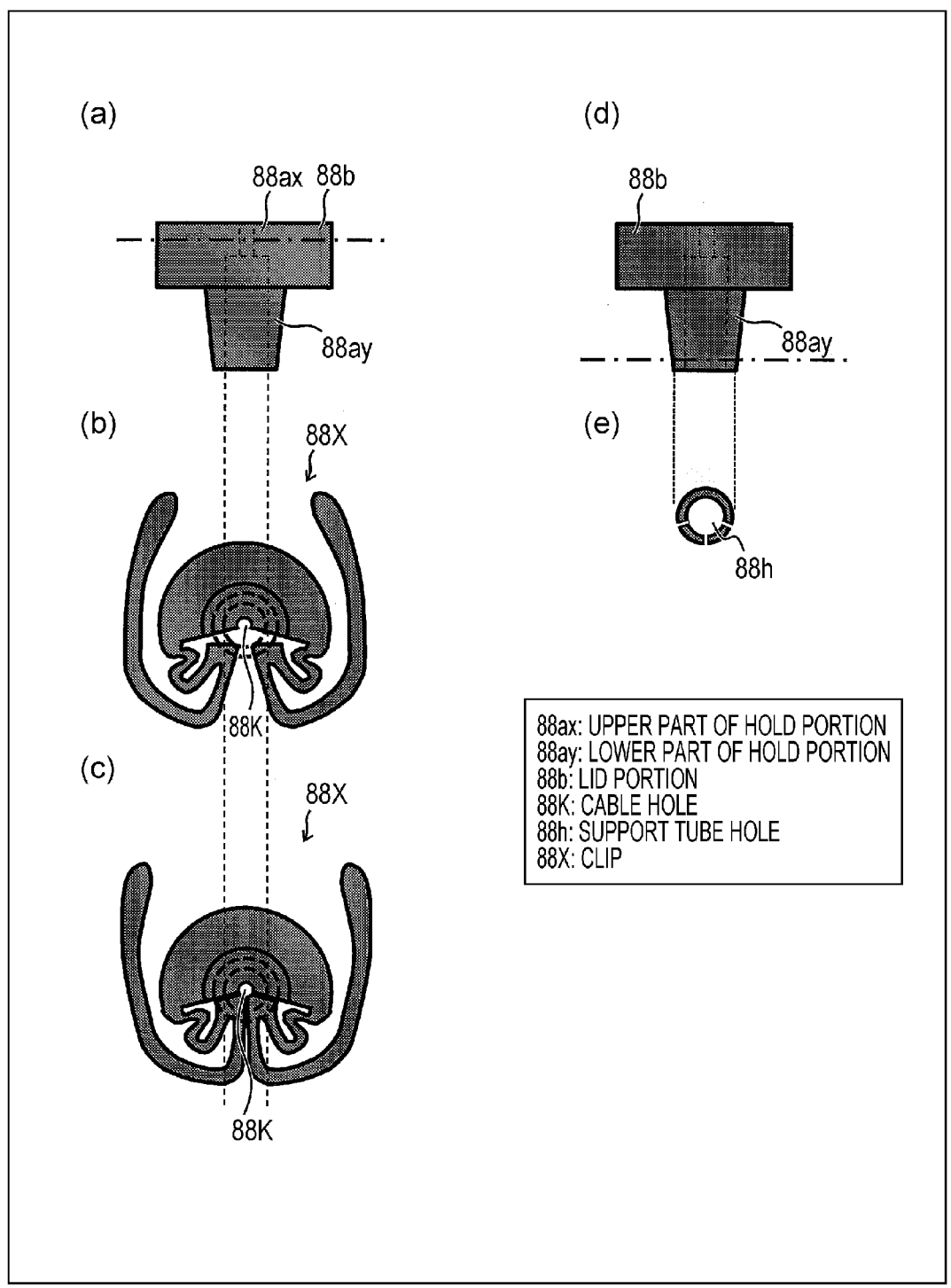
FIGS. 21(a) to 21(e) are configuration views illustrating a modification example of the air plug of FIG. 20.
Figure 22:
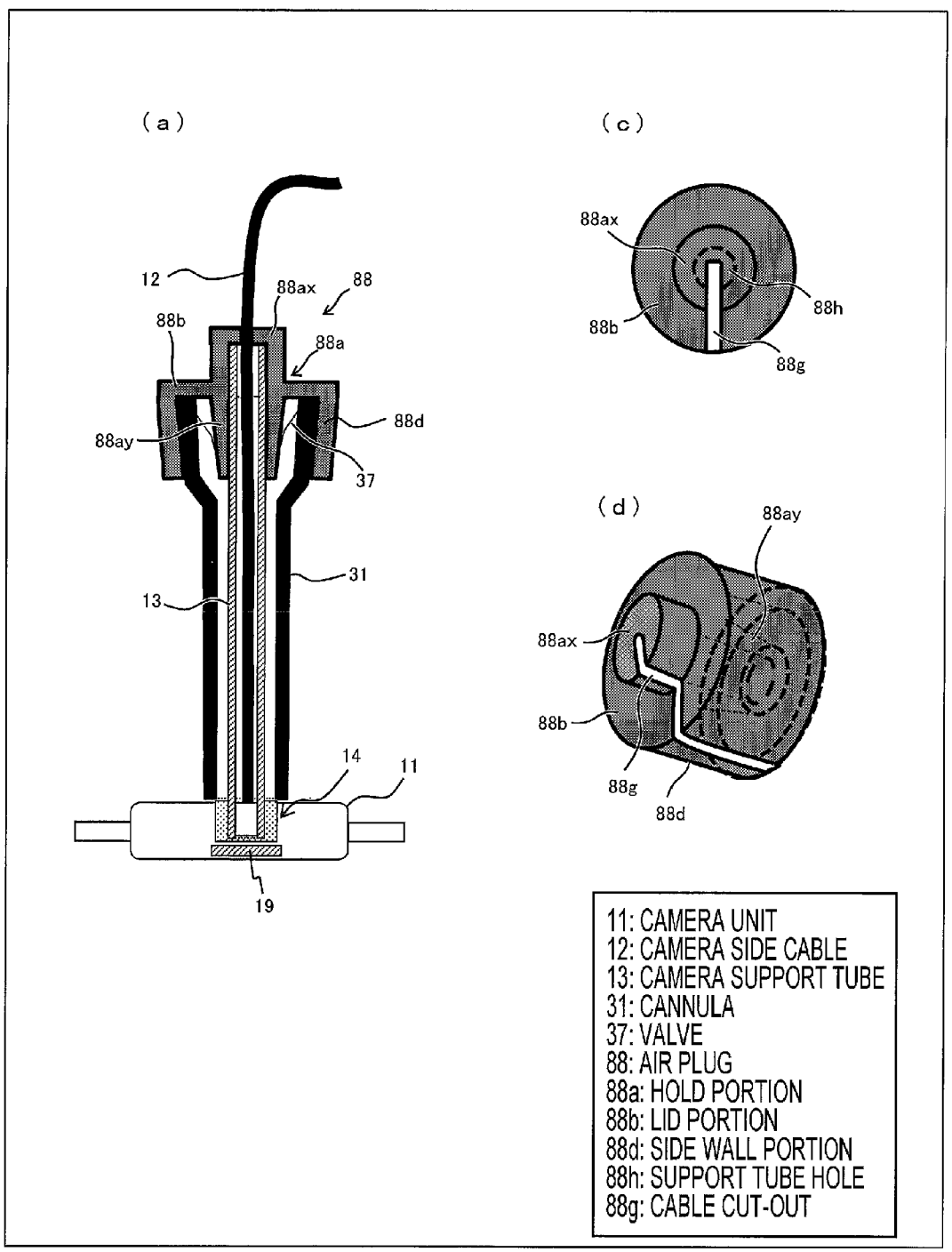
FIGS. 22(a) to 22(d) are configuration views illustrating a structure of the air plug (having a function of the support tube holder and the cable holder) according to Embodiment 6.

FIGS. 21(a) and 21(d) are longitudinal sectional views of modification examples of the air plug. FIGS. 21(b) and 21(c) are lateral sectional views of a part illustrated by a dashed line of FIG. 21(a). FIG. 21(e) is a lateral sectional view of a part illustrated by a dashed line of FIG. 21(d). As illustrated in FIG. 21, a structure in which a clip 88X, such as a plate spring, which includes a cable hole 88K is used in the upper part 88ax of the hold portion 88a and lid portion 88b, and the camera side cable 12 in the cable hole 88K is nipped from the side surface by opening (FIG. 21(b)) and closing (FIG. 21(c)) of the clip 88X, is employed. In addition, the lower end of the hold portion 88a has a ring shape similar to FIG. 21(e). According to such a clip structure, it is possible to obtain a stabilized cable holding force, and to employ various types of cannulas having different sizes from each other, and versatility is improved.

<Air Plug-cum-Support Tube Holder-cum-Cable Holder>

The air plug can also function as the support tube holder which holds and fixes the support tube to the cannula, and the cable holder which holds and fixes the camera side cable to the support tube.

FIG. 22(a) is a sectional view illustrating a state where the air plug having a function of the support tube holder and the cable holder is provided between the end part outside the body in the camera support tube 13 and the end part outside the body in the cannula 31, in a sectional view illustrating the joined state of the camera support tube 13 inserted into the cannula 31 and the camera unit 11. FIG. 22(c) is an upper view of the air plug. FIG. 22(d) is a perspective view of the air plug.

As illustrated in FIGS. 22(a), 22(c) and 22(d), the air plug 88 (accessory for the support tube, support tube holder, cable holder) includes the hold portion 88a, the flange-like lid portion 88b, and the side wall portion 88d which extends to the body surface side from the circumferential edge of the lid portion 88b, the hold portion 88a includes the upper part 88ax positioned above the lid portion 88b in a columnar shape and the lower part 88ay positioned below the lid portion 88b (body surface side) in a shape of a tapered (becomes narrow when approaching the body surface side) truncated cone, the support tube hole 88h is provided in the hold portion 88a, and a cable cut-out 88g which reaches the lower end of the side wall portion 88d via the circumferential edge of the lid portion 88b from the center part of the upper part 88ax. The air plug 88 configured of an elastic member, such as one made of rubber, is disposed to be fitted into the upper end part of the cannula 31 (tube-like member) so that the lower part 88ay pressingly expands the valve 37, and to cover the upper surface of the upper end part of the cannula 31 with the lid portion 88b and to cover the outer side surface of the upper end part of the cannula 31 with the side wall portion 88d, in a state where the camera side cable 12 which passes through the cable cut-out 88g is held at the center of the upper part 88ax, and the camera support tube 13 is held in the support tube hole 88h. As described above, the air plug 88 substantially blocks the void between the cannula 31 and the camera support tube 13, and fixes each of the camera support tube 13, the cannula 31, and the camera side cable 12.

Figure 23:
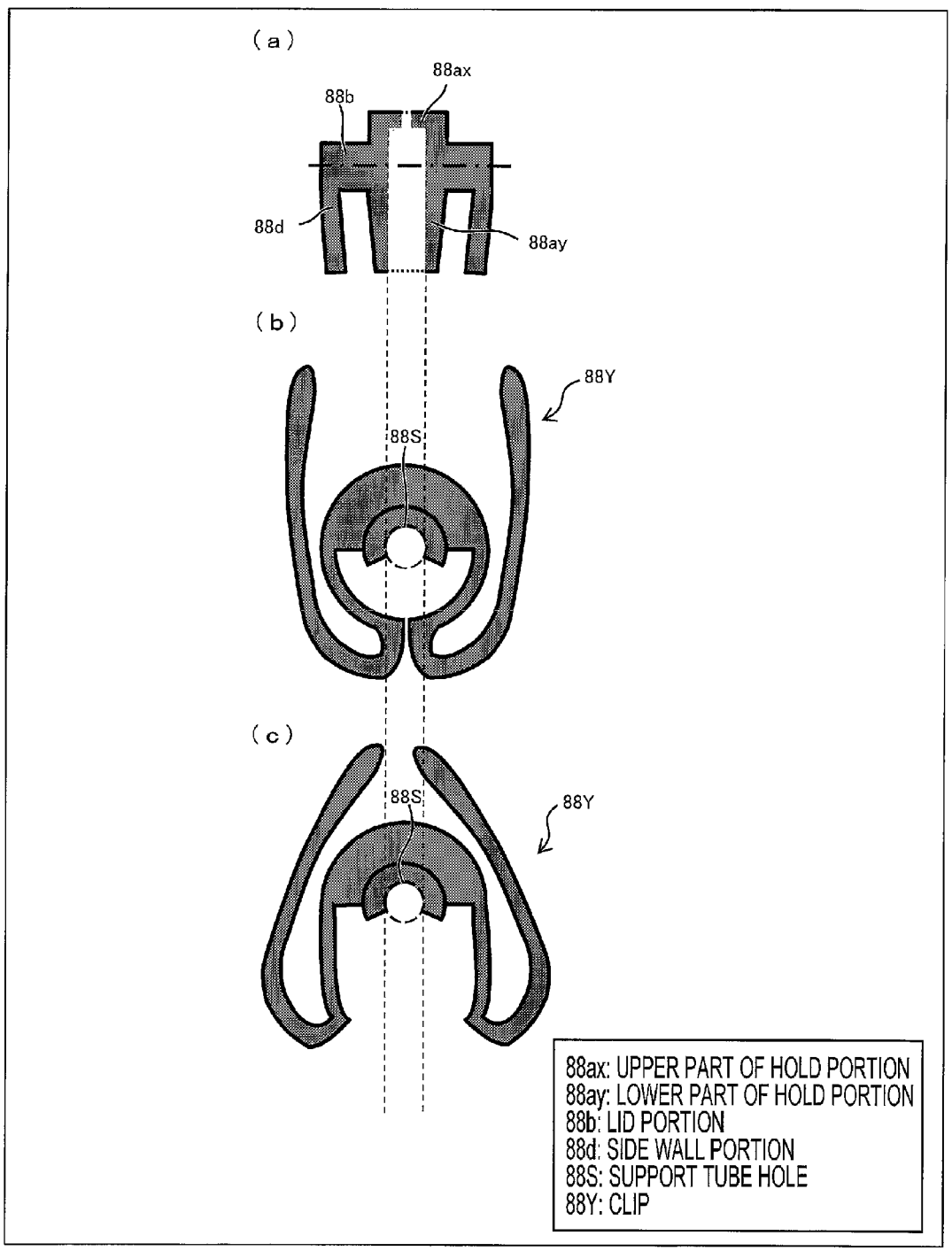
FIGS. 23(a) to 23(c) are configuration views illustrating a modification example of the air plug of FIG. 22.

FIG. 23(a) is a longitudinal sectional view of a modification example of the air plug. FIGS. 23(b) and 23(c) are lateral sectional views of a part illustrated by a dashed line of FIG. 23(a). As illustrated in FIG. 21, a structure in which the clip 88X, such as a plate spring, which includes the cable hole 88K is used in the upper part 88ax of the hold portion 88a of FIG. 23, and the camera side cable 12 in the cable hole 88K is nipped from the side surface by opening and closing the clip 88X, is employed. According to such a clip structure, it is possible to obtain a stabilized cable holding force, and to employ various types of camera side cables having different sizes from each other, and versatility is improved.

In addition, as illustrated in FIGS. 23(a) to 23(c), a structure in which a clip 88Y, such as a plate spring, which includes a support tube hole 88S is used in the upper part 88ax and the lid portion 88b of the hold portion 88a, and the camera support tube 13 in the tube hole 88S is nipped from the side surface by opening and closing the clip 88Y, is employed. According to such a clip structure, it is possible to obtain a stabilized cable holding force.

Furthermore, a cable holder made of the clip 88X of FIG. 21 is provided at the upper part 88ax of the hold portion 88a, the lower end of the hold portion 88a has a ring shape illustrated in FIG. 21(e), and as illustrated in FIG. 23, the clip 88Y which fixes the camera support tube 13 can be provided therebetween. According to such a double clip structure, it is possible to obtain a stabilized cable holding force of the camera support tube and the camera side cable, and to employ various types of camera side cables, camera support tubes, and cannulas (tube-like members) having different sizes from each other, and versatility is improved.

In Embodiment 6, the air plug 88 which can be used in fixing the camera support tube 13, the camera side cable 12, and the cannula 31, will be described. However, the embodiment is not limited thereto, and it is needless to say that the structures described in Embodiments 1 to 4 may be used.

[Regarding each of Above-described Embodiments]

The cannula described in each of the above-described embodiments is merely an example of the tube-like member (tube-like device), and the cannula can be used instead of the trocar which is the same tube-like member (tube-like device).

CONCLUSION

A camera system for monitoring the inside of a body (1) according to aspect 1 of the present invention includes: a support tube (camera support tube 13) of which one end part 13a is inserted into the body; an imaging unit (camera unit 11) which includes a joining portion (support tube joining portion 14) which joins with the support tube, and joins with the support tube in the body; a cable (camera side cable 12) which is connected to the imaging unit, and is drawn out toward the outside of the body through the support tube; a control system (3) which is on the outside of the body, is connected to the cable, and includes at least a display apparatus (display 18); a fixing tool (for example, string-like member 38, adhesive tape 46, fixing devices 141, 151, 161, and 171) which directly or indirectly fixes the support tube to a body surface in a state where a length of the support tube in the body, a rotational direction of the support tube, and an inclination of the support tube with respect to the body surface, which are set by a practitioner, are held.

In the camera system for monitoring the inside of a body (1) according to aspect 2 of the present invention, in the above-described aspect 1, a cannula (cannula 31) having a tube-like structure into which the support tube is insertable may further be provided, and the support tube may be fixed to the body surface in a state of being inserted into the cannula.

In the camera system for monitoring the inside of a body (1) according to aspect 3 of the present invention, in the above-described aspect 2, the support tube may be fixed to the cannula outside the body, and the fixing tool may fix the support tube by fixing the cannula to the body surface.

In the camera system for monitoring the inside of a body (1) according to aspect 4 of the present invention, in the above-described aspect 2 or 3, the support tube may be movable in an axial direction within a range that the length of the support tube allows, and may be fixed to the cannula to be rotatable around an axis.

In the camera system for monitoring the inside of a body (1) according to aspect 5 of the present invention, in any of the above-described aspects 2 to 4, the support tube may be fixed to the cannula due to a biasing force.

In the camera system for monitoring the inside of a body (1) according to aspect 6 of the present invention, in any of the above-described aspects 2 to 5, fixing strength between the support tube and the cannula is greater than joining strength between the support tube and the joining portion.

In the camera system for monitoring the inside of a body (1) according to aspect 7 of the present invention, in any of the above-described aspects 2 to 6, the fixing strength between the support tube and the cannula is within a range of 5 N to 50 N.

In the camera system for monitoring the inside of a body (1) according to aspect 8 of the present invention, in any of the above-described aspects 1 to 5, a cable holder (cable fastener 43, air plug 88) which holds and fixes the cable to the support tube is provided, and the support tube or the cable is fixed to the outside of the body.

In the camera system for monitoring the inside of a body (1) according to aspect 9 of the present invention, in any of the above-described aspects 1 to 8, a cable holder which holds and fixes the cable to the support tube is provided, and cable holding strength of the cable holder is greater than joining strength between the support tube and the joining portion.

In the camera system for monitoring the inside of a body (1) according to aspect 10 of the present invention, in the above-described aspect 9, the joining strength is within a range of 3 N to 6 N.

In the camera system for monitoring the inside of a body (1) according to aspect 11 of the present invention, in the above-described aspect 9, the fixing strength onto the body surface by the fixing tool is greater than the cable holding strength.

In the camera system for monitoring the inside of a body (1) according to aspect 12 of the present invention, in any of the above-described aspects 1 to 11, a cable holder (cable fastener 43, air plug 88) which holds and fixes the cable to the support tube is provided, and cable holding strength of the cable holder is within a range of 5 N to 50 N.

In addition, in the aspects 8 to 12 of the present invention, in a case where the support tube is inserted into the cannula, the cable holder may have a function of blocking at least a part of a void between the support tube and the cannula.

In the camera system for monitoring the inside of a body (1) according to aspect 13 of the present invention, in any of the above-described aspects 2 to 7, the cable holder which holds and fixes the cable to the support tube or a support tube holder which holds and fixes the support tube to the cannula, is provided, and the cable holder or the support tube holder has a function of blocking at least a part of a void between the support tube and the cannula.

An accessory for a support tube (88) of the camera system for monitoring the inside of a body (1) according to aspect 14 of the present invention, is an accessory for a support tube of the camera system for monitoring the inside of a body described in any one of the above-described aspects 2 to 7, which has at least two functions among a function of fixing the cable to the support tube, a function of fixing the support tube to the cannula, and a function of blocking at least a part of the void between the support tube and the cannula.

A fixing tool (adhesive tape 46) for a camera system for monitoring the inside of a body (1) according to aspect 15 of the present invention includes a flexible adhesion surface with respect to the body surface.

A method for installing a camera system for monitoring the inside of a body according to aspect 16 of the present invention, includes: a step of inserting a cable (camera side cable 12) connected to a control system (3) which has at least a display apparatus (display 18) on the outside of the body, and an imaging unit (camera unit 11) connected to the cable, into the body; a step of drawing out the cable toward the outside of the body through a support tube (camera support tube 13) of which one end part 13a is inserted into the body; a step of joining the imaging unit and the support tube to each other at a joining portion (support tube joining portion 14) provided in the imaging unit, in the body; and a step of adjusting a length of the support tube in the body, a rotational direction of the support tube, an inclination of the support tube with respect to the body surface in the body, and directly or indirectly fixing the support tube to the body surface.

(Additional Expression of Present Invention)

The present invention can be expressed as follows.

The camera system for monitoring the inside of a body (1) according to an aspect of the present invention, includes: a support tube (camera support tube 13) of which one end part 13a is inserted into a body; an imaging unit (camera unit 11) which includes a joining portion (support tube joining portion 14) which joins with the support tube, and joins with the support tube in the body; a cable (camera side cable 12) which is connected to the imaging unit, and is drawn out toward the outside of the body through the support tube; and a control system (3) which is on the outside of the body, is connected to the cable, and includes at least a display apparatus (display 18), and in the support tube, it is possible to arbitrarily change the direction of the visual field of the imaging unit and the rotational direction of the visual field in the body, to arbitrarily change the imaging zoom (distance to the object) to be within an allowable range of the length of the support tube, and to directly or indirectly fix the support tube to the body surface.

In the camera system for monitoring the inside of a body (1), the cannula 31 for making the support tube pass through the inside thereof, may be used.

In the camera system for monitoring the inside of a body (1), the support tube can be fixed to the body surface as the support tube is locked to the trocar 32 in the periphery by the string-like fixing tool (string-like member 38).

In the camera system for monitoring the inside of a body (1), the support tube can be fixed to the body surface by using a dedicated device (for example, fixing devices 141 and 161) having adhesiveness at the contact part with the body surface.

In the camera system for monitoring the inside of a body (1), the support tube can be fixed to the body surface by using a dedicated device (for example, fixing device 151) which is fixed to the body surface by nipping the skin at the contact surface with the body surface.

In the camera system for monitoring the inside of a body (1), the support tube can be fixed to the body surface by receiving the restoring force 49 generated by elasticity of the body wall when inserting the support tube into the body wall and inclining the angle, and by using a dedicated device (for example, fixing devices 161 and 171) which uses the pressing force as a force (for example, body wall pressing force 50) which presses the body wall at the contact part with the body surface.

In the camera system for monitoring the inside of a body (1), the support tube can be fixed to the body surface by using a dedicated device of which one end is fixed to the operating table.

In the camera system for monitoring the inside of a body (1), the support tube can be fixed to the body surface by using a tape (adhesive tape 46).

In the camera system for monitoring the inside of a body (1), the support tube can lock the cable, and can be fixed to the body surface by fixing the cable to the body surface.

In the camera system for monitoring the inside of a body (1), the support tube can be fixed to the cannula outside the body, and can be fixed to the body surface by fixing the cannula to the body surface.

The present invention is not limited to the above-described embodiments, and also includes an embodiment which can be obtained by appropriately changing and combining the above-described embodiments based on common technical knowledge.

INDUSTRIAL APPLICABILITY

An imaging apparatus is appropriate for endoscopic surgery or the like.

REFERENCE SIGNS LIST

1 CAMERA SYSTEM FOR MONITORING INSIDE OF BODY
2 IMAGING APPARATUS
3 CONTROL SYSTEM
4 OPERATION UNIT
11 CAMERA UNIT
12 CAMERA SIDE CABLE
13 CAMERA SUPPORT TUBE
13a, 13b END PART
14 SUPPORT TUBE JOINING PORTION
15 CABLE CONNECTOR
16 INSTRUMENT SIDE CABLE
17 CAMERA UNIT CONTROL INSTRUMENT
18 DISPLAY
19 CIRCUIT BOARD
21 CAMERA HOUSING
22 SUPPORTING PORTION
23 LOCKING FEMALE SCREW
24 IMAGING UNIT
25 SOLID-STATE IMAGING DEVICE
26 LENS
27 ILLUMINATION APPARATUS
28 CONTROL CIRCUIT
31 CANNULA
31a, 31b END PART
32, 32a to 32c TROCAR
33, 33a to 33c FORCEPS
34 ENDOSCOPE
36 OBTURATOR
37 VALVE
38 STRING-LIKE MEMBER (FIXING TOOL)
41 BODY WALL
41a to 41c PORT
42 ORGAN
43 CABLE FASTENER (CABLE HOLDER)
43a LONGITUDINAL GROOVE
45 BODY SURFACE
46 ADHESIVE TAPE (FIXING TOOL)
49 RESTORING FORCE
50 BODY WALL PRESSING FORCE
77 STOPPER
88 AIR PLUG (ACCESSORY FOR SUPPORT TUBE, CABLE HOLDER, SUPPORT TUBE HOLDER)
113 HEAD PORTION
114 LEG PORTION
117 ENDOSCOPE CONTROL INSTRUMENT
118 DISPLAY
123 LOCKING HOLE
131 HEAD PORTION
132 LEG PORTION
141 FIXING DEVICE (FIXING TOOL)
144 SUPPORT TABLE
145 BAND
145a FIXING END
146 ADJUSTER
151 FIXING DEVICE (FIXING TOOL)
152 SUPPORT TABLE
153 CLIP PORTION
154 SUPPORT TUBE MOUNTING UNIT
155 ARM UNIT
156 CLAMP PORTION
157 SCREW FASTENING HANDLE
161 FIXING DEVICE (FIXING TOOL)
162 SUPPORT TABLE
163 SUPPORT TUBE MOUNTING UNIT
164 ARM UNIT
165 CLAMP PORTION
166 SCREW FASTENING HANDLE
171 FIXING DEVICE (FIXING TOOL)
172 ARM UNIT
173 CLAMP PORTION
174 LINKING PORTION
223 SLIT
323 LOCKING HOLE
423 LOCKING CLAW
523 LOCKING CLAW
623 LOCKING HOLE

The invention claimed is:
1. A camera system for monitoring the inside of a body, comprising:
a support tube of which one end part is insertable into the body;

an imaging unit which includes a joining portion which joins with the support tube, and is joinable with the support tube in the body;
a cable which is connected to the imaging unit, and is drawn out toward the outside of the body through the support tube;
a control system which is outside of the body, is connected to the cable, and includes at least a display apparatus; and
a mechanism that maintains a length of the support tube in the body, a rotational direction of the support tube, and an inclination of the support tube with respect to the body surface, which are set by a practitioner, wherein
the mechanism includes a cannula having a tube-like structure into which the support tube is insertable,
one end part of the cannula is insertable into the body,
the support tube is inserted into the cannula,
the support tube is held by the cannula outside the body, and
the mechanism includes a cable holder which holds and fixes the cable to the support tube, and the cable holder has a function of blocking at least a part of a void between the support tube and the cannula.

2. The camera system for monitoring the inside of a body according to claim 1,
wherein the support tube is movable in an axial direction within a range that the length of the support tube allows, and is held by the cannula to be rotatable around an axis.

3. The camera system for monitoring the inside of a body according to claim 1,
wherein the support tube is held by the cannula due to a biasing force.

4. The camera system for monitoring the inside of a body according to claim 1,
wherein a fixing strength between the support tube and the cannula is greater than a holding strength of the joining portion.

5. The camera system for monitoring the inside of a body according to claim 1,
wherein a holding strength of the cannula is within a range of 5 N to 50 N.

6. The camera system for monitoring the inside of a body according to claim 1,
wherein a cable holding strength of the cable holder is greater than a joining strength between the support tube and the joining portion.

7. The camera system for monitoring the inside of a body according to claim 6,
wherein the joining strength is within a range of 3 N to 6 N.

8. The camera system for monitoring the inside of a body according to claim 1,
wherein a cable holding strength of the cable holder is within a range of 5 N to 50 N.

9. An accessory for a support tube of a camera system for monitoring the inside of a body,
the camera system comprising:
a support tube of which one end part is insertable into the body;
an imaging unit which includes a joining portion which joins with the support tube, and is joinable with the support tube in the body;
a cable which is connected to the imaging unit, and is drawn out toward the outside of the body through the support tube;
a control system which is outside of the body, is connected to the cable, and includes at least a display apparatus; and
a mechanism that maintains a length of the support tube in the body, a rotational direction of the support tube, and an inclination of the support tube with respect to the body surface, which are set by a practitioner, wherein
the mechanism includes a cannula having a tube-like structure into which the support tube is insertable,
one end part of the cannula is insertable into the body,
the support tube is inserted into the cannula,
the support tube is held by the cannula outside the body, and
the accessory has a function of holding the cable with the support tube and a function of blocking at least a part of the void between the support tube and the cannula.

* * * * *